(12) United States Patent
Kim

(10) Patent No.: US 9,795,760 B2
(45) Date of Patent: *Oct. 24, 2017

(54) MOTION SICKNESS REDUCTION

(76) Inventor: Samuel Kim, Englewood Cliffs, NJ (US)

(*) Notice: Subject to any disclaimer, the term of this patent is extended or adjusted under 35 U.S.C. 154(b) by 3374 days.

This patent is subject to a terminal disclaimer.

(21) Appl. No.: 11/286,679

(22) Filed: Nov. 22, 2005

(65) Prior Publication Data

US 2006/0079729 A1 Apr. 13, 2006

Related U.S. Application Data

(63) Continuation-in-part of application No. 11/166,483, filed on Jun. 24, 2005, now Pat. No. 7,722,526.

(60) Provisional application No. 60/588,710, filed on Jul. 16, 2004, provisional application No. 60/630,055, filed on Nov. 22, 2004.

(51) Int. Cl.
*A61M 21/00* (2006.01)
*A61M 21/02* (2006.01)

(52) U.S. Cl.
CPC .......... *A61M 21/00* (2013.01); *A61M 21/02* (2013.01); *A61M 2021/005* (2013.01)

(58) Field of Classification Search
CPC .................................................. A61M 21/00
USPC ................ 600/27, 28; 345/649; 382/104
See application file for complete search history.

(56) References Cited

U.S. PATENT DOCUMENTS

| | | |
|---|---|---|
| 2,334,018 A | 11/1943 | Mayne |
| 4,929,228 A | 5/1990 | Hendricks |
| 4,930,435 A | 6/1990 | Newman |
| 5,067,941 A | 11/1991 | Hendricks |
| 5,161,196 A | 11/1992 | Ferguson |
| 5,386,285 A * | 1/1995 | Asayama ............ 356/4.01 |
| 5,647,835 A | 7/1997 | Martineau |
| 5,966,680 A | 10/1999 | Butnaru |
| 6,042,533 A | 3/2000 | Kania |
| 6,228,021 B1 | 5/2001 | Kania |
| 6,275,998 B1 | 8/2001 | Tromble |
| 6,443,913 B1 | 9/2002 | Kania |
| 6,497,649 B2 | 12/2002 | Parker et al. |
| 6,663,155 B1 | 12/2003 | Malone et al. |
| 6,692,428 B1 | 2/2004 | Kania |
| 6,719,343 B2 | 4/2004 | Emerling et al. |

(Continued)

OTHER PUBLICATIONS

Michael J. Griffen and Maria M. Newman, "Visual Field Effects on Motion Sickness in Cars", Aviation, Space, and Environmental Medicine, Sep. 2004, vol. 75, No. 9.

(Continued)

*Primary Examiner* — Christine H Matthews
(74) *Attorney, Agent, or Firm* — Bergman & Song LLP; Michael Bergman

(57) ABSTRACT

Methods, apparatuses and systems for enabling a passenger in a moving vehicle to read text or view an image while avoiding or reducing the symptoms of motion sickness, by providing the passenger a view of the text or image simultaneously with a view of external stationary reference points. The methods, apparatuses, and systems, in some embodiments, include the use of a transparent medium which can display text or images. Other embodiments include a video camera capturing video images and substantially simultaneously displaying such images together with text or images on a means of display.

5 Claims, 21 Drawing Sheets

(56) References Cited

U.S. PATENT DOCUMENTS

| | | | |
|---|---|---|---|
| 6,866,225 B2 | 3/2005 | Jones et al. | |
| 6,947,071 B2 * | 9/2005 | Eichmann | 348/142 |
| 7,046,259 B2 | 5/2006 | Humphries | |
| 7,135,961 B1 * | 11/2006 | Operowsky et al. | 340/425.5 |
| 2001/0000459 A1 | 4/2001 | Kania | |
| 2002/0163215 A1 | 11/2002 | Emerling et al. | |
| 2004/0101165 A1 * | 5/2004 | Gallo et al. | 382/104 |
| 2004/0102676 A1 * | 5/2004 | Brendley et al. | 600/27 |
| 2004/0217234 A1 | 11/2004 | Jones et al. | |
| 2004/0217976 A1 | 11/2004 | Sanford | |
| 2004/0217978 A1 | 11/2004 | Humphries | |
| 2004/0241624 A1 * | 12/2004 | Sudo | 434/118 |

OTHER PUBLICATIONS

Patricia M. Bercham, "Motion Sickness Literature Search", Army Research Laboratory, ARL-MR-504, May 2002.
File History for U.S. Appl. No. 60/851,984.
File History for U.S. Appl. No. 60/588,710.
File History for U.S. Appl. No. 11/166,483.
File History for U.S. Appl. No. 60/844,424.
File History for PCT Serial No. PCT/US2007/020068.
File History for U.S. Appl. No. 12/381,612.

* cited by examiner

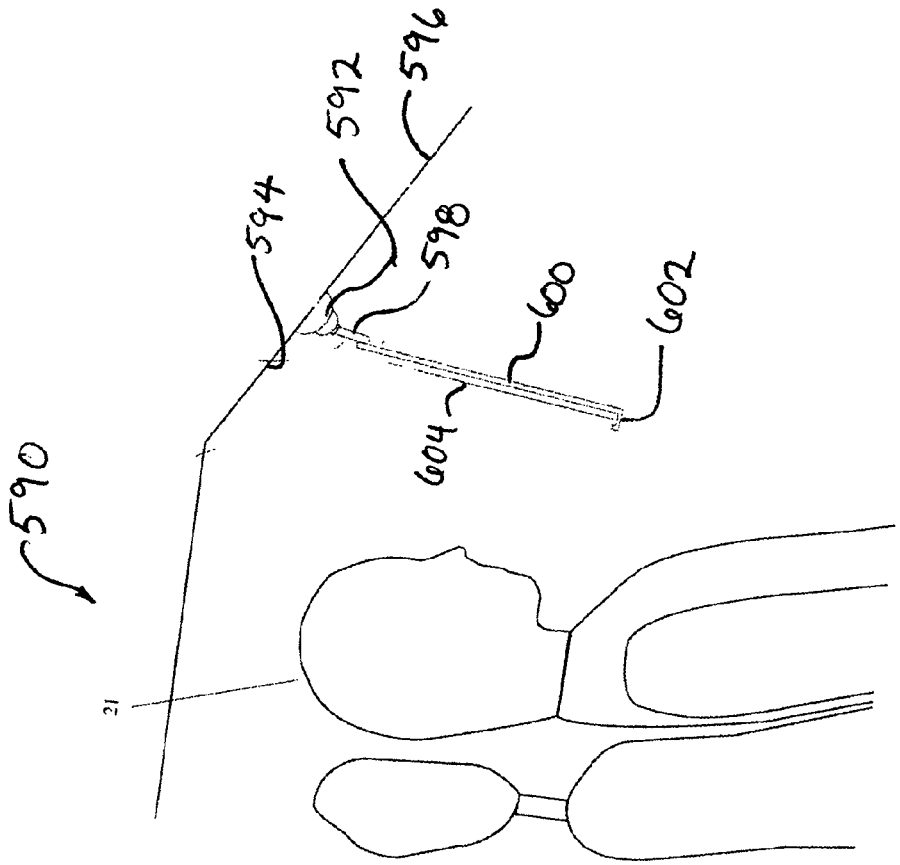
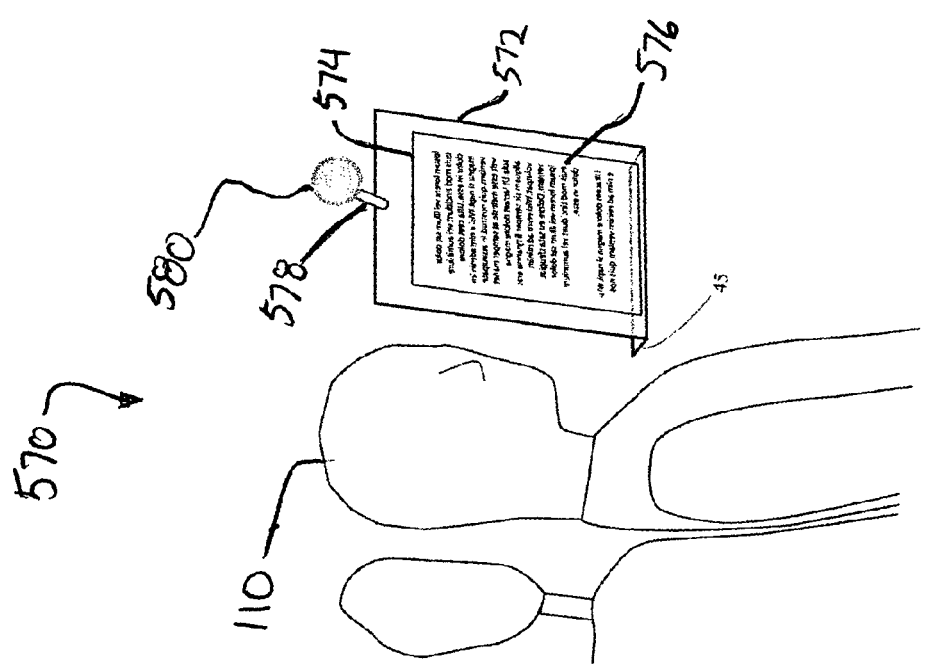

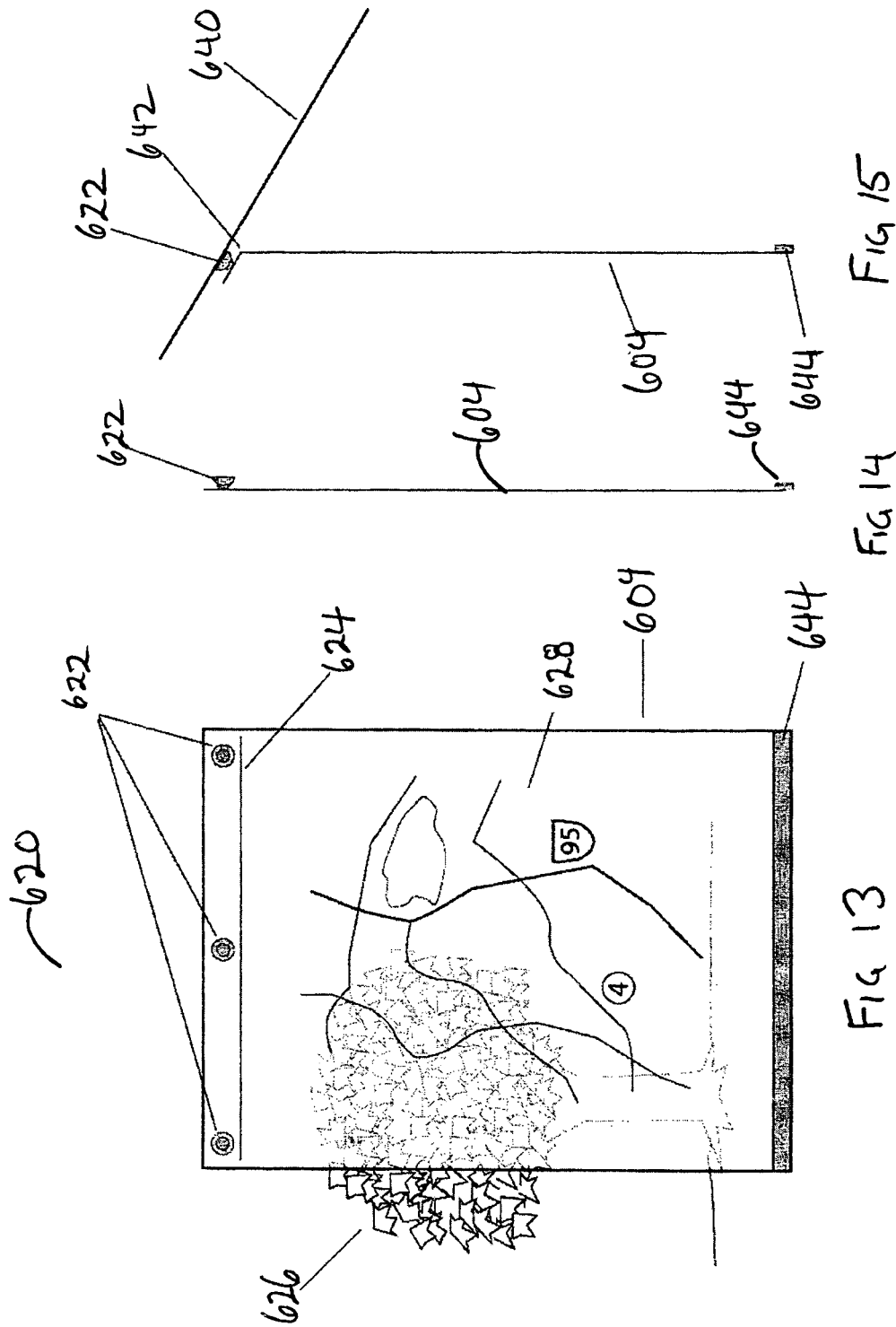

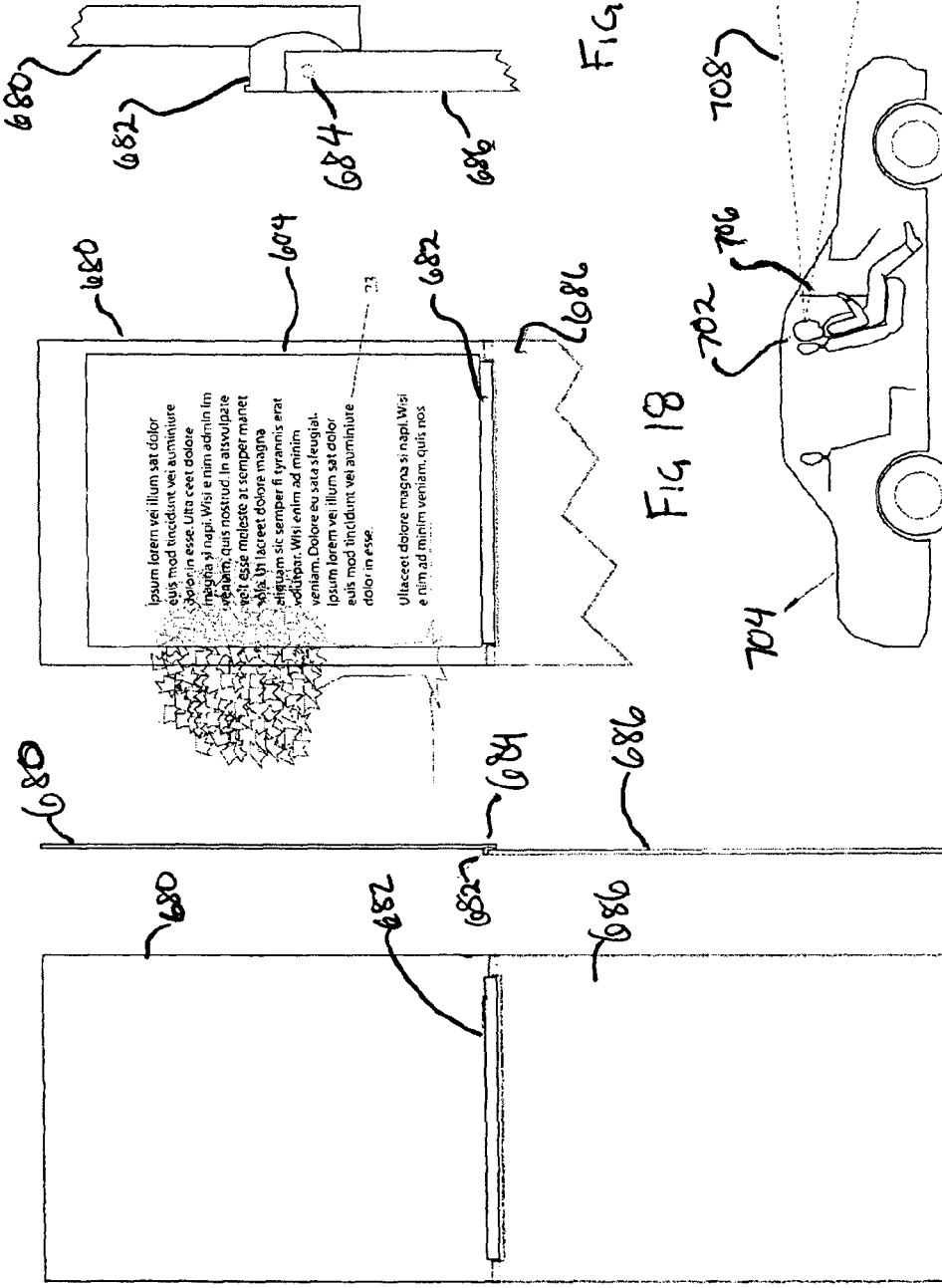

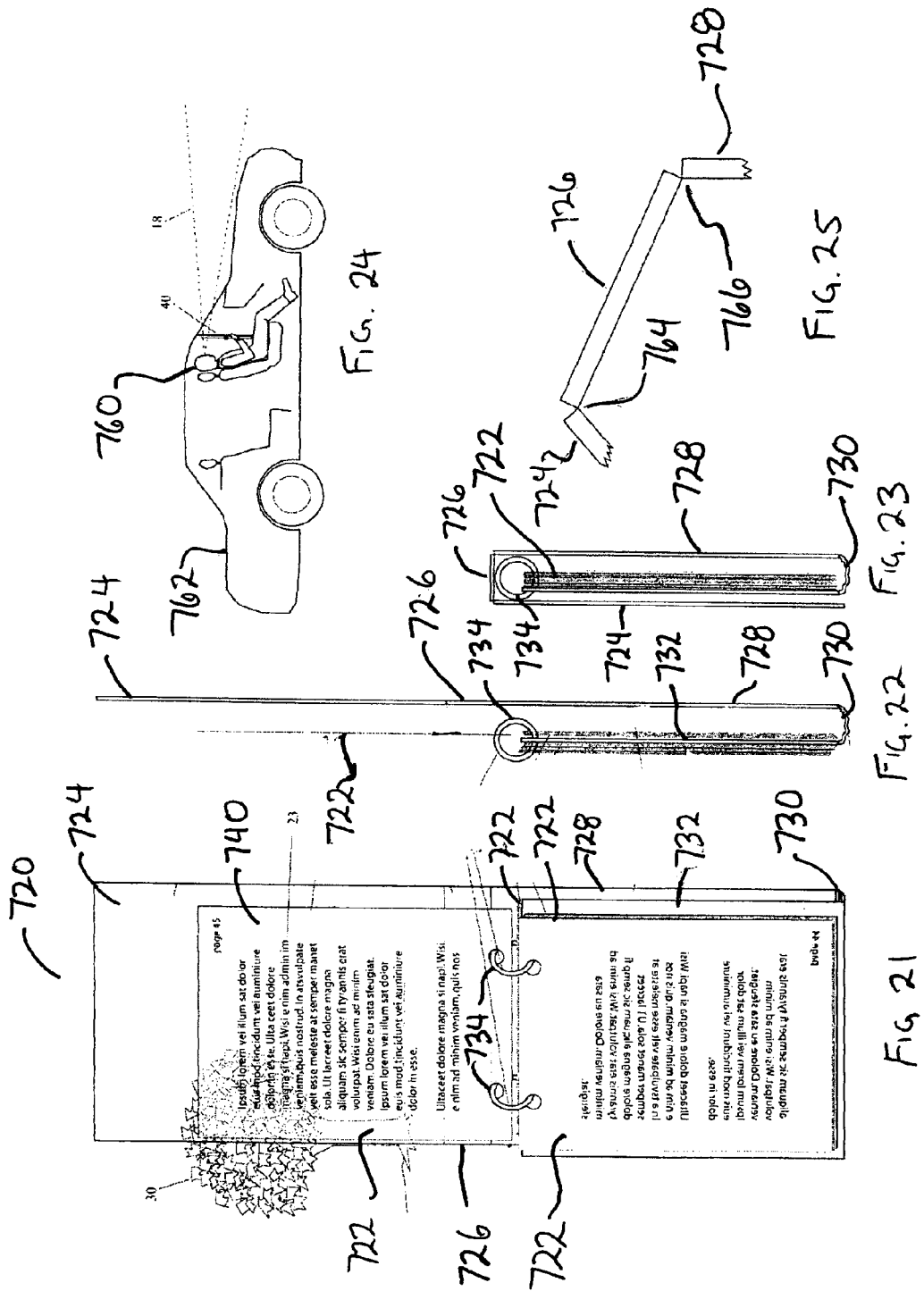

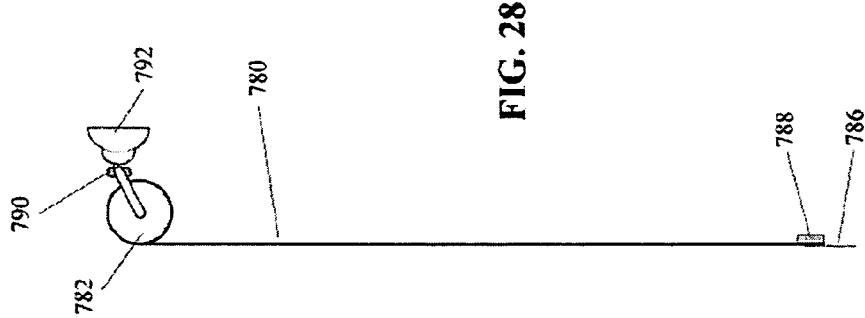
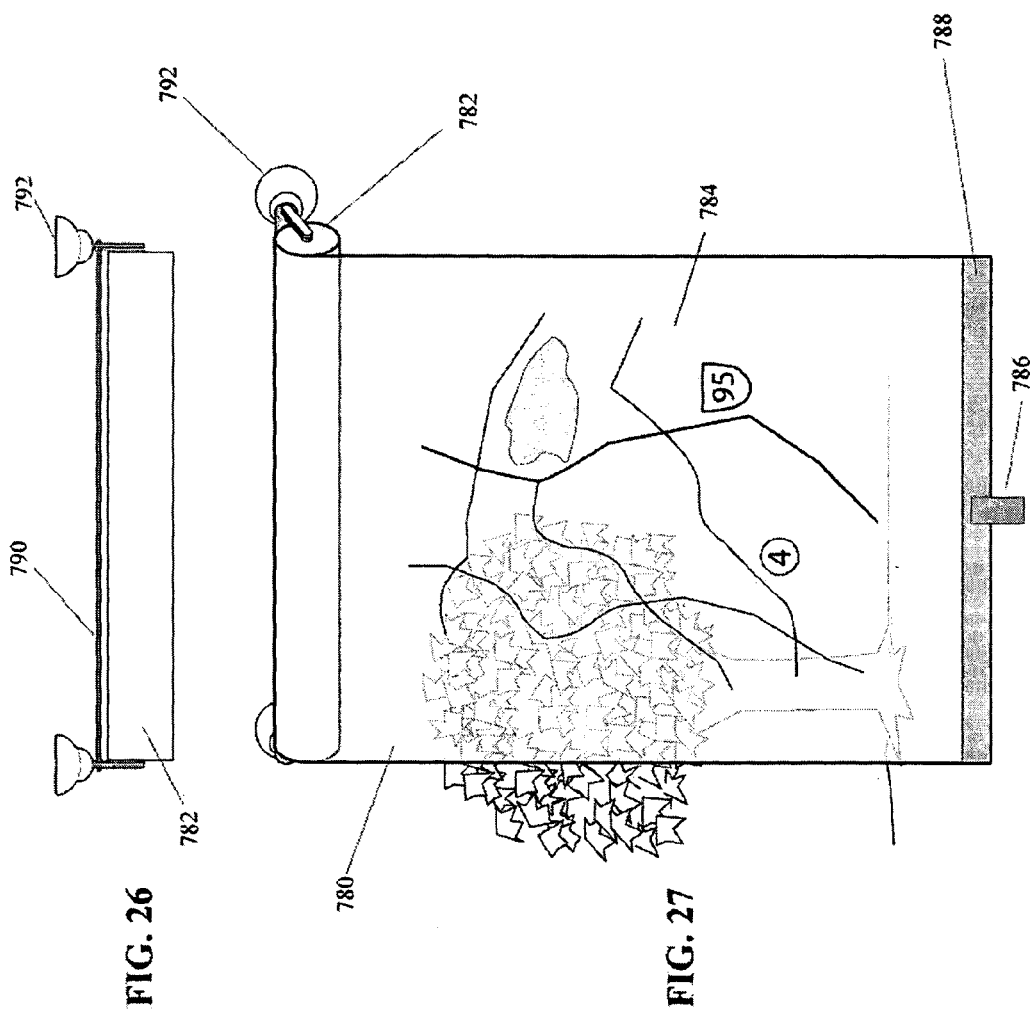
FIG. 26
FIG. 27
FIG. 28

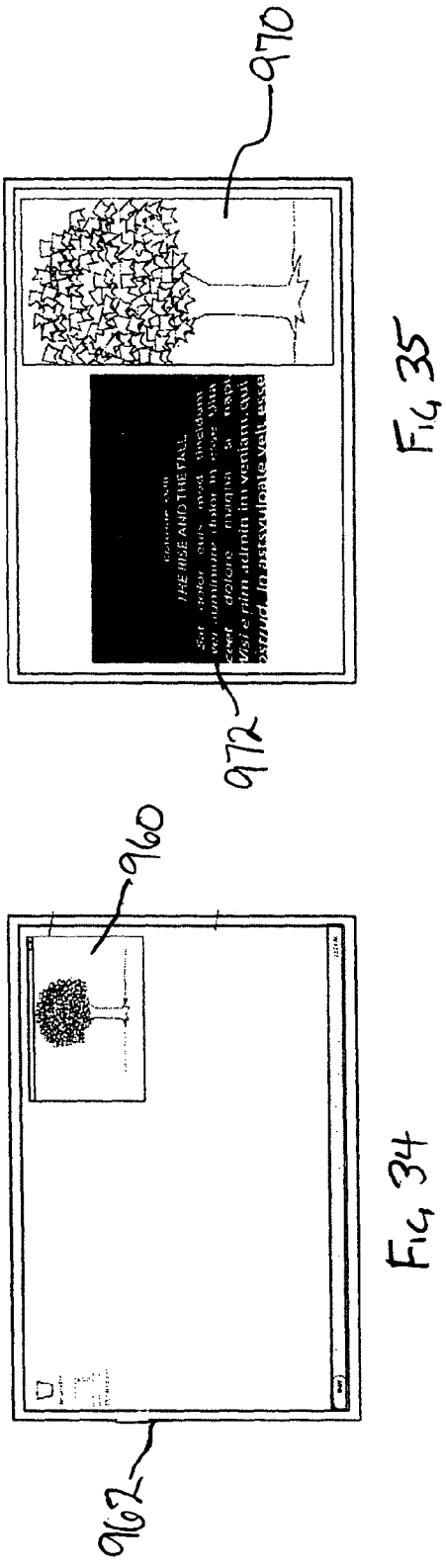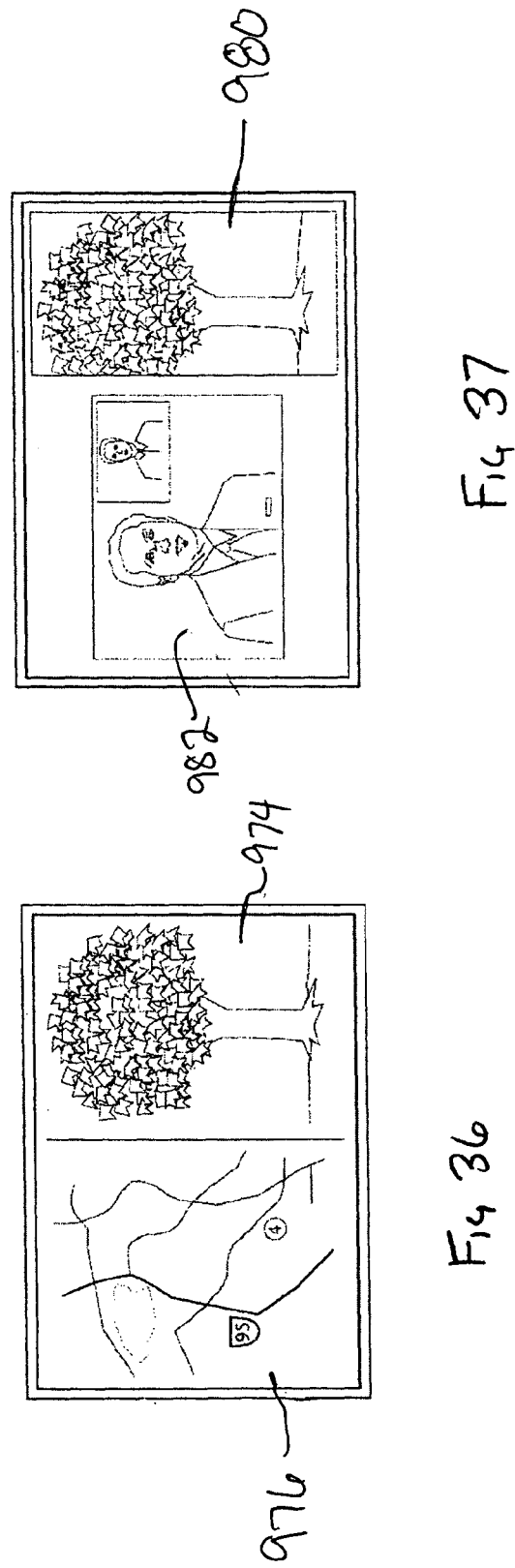

MOTION SICKNESS REDUCTION

CROSS-REFERENCE TO RELATED APPLICATIONS

This application claims the benefit of U.S. Provisional Patent Application No. 60/630,055, entitled, "METHOD OF PREVENTING MOTION SICKNESS WHILE READING TEXT OR VIEWING AN IMAGE", filed Nov. 22, 2004, the disclosure of which is herewith incorporated by reference in its entirety; and this application is a continuation in part of U.S. non-provisional patent application Ser. No. 11/166,483 filed Jun. 24, 2005 now U.S. Pat. No. 7,722,526 entitled System, Method and Apparatus for Preventing Motion Sickness, the disclosure of which is herewith incorporated by reference in its entirety, which non-provisional patent application claims the benefit of U.S. Provisional Patent Application No. 60/588,710, entitled, "METHOD OF PREVENTING MOTION SICKNESS", filed Jul. 16, 2004.

BACKGROUND OF THE INVENTION

The present invention relates generally to a method, apparatus, and system to allow a passenger in a moving vehicle to read text or view an image while reducing or preventing motion sickness.

Motion sickness relates to the sense of balance, equilibrium and spatial orientation. The sense of balance is controlled and maintained by an intricate interaction of multiple parts of the human body, specifically, the inner ears (also called the labyrinth), the eyes, skin pressure receptors, muscle and joint sensory receptors, and the central nervous system.

The inner ears monitor motion, such as turning and tilting. The eyes monitor body orientation in space (i.e. upside down, right side up, etc.) and also directions of motion. The skin pressure receptors, such as those in the joints and spine, determine what part of the body is down and touching the ground or other surfaces. The muscle and joint sensory receptors determine which parts of the body are moving. The central nervous system (the brain and spinal cord), processes all of the information from the four other systems to determine the spatial orientation and motion of the body.

People may get motion sickness when their brains receive conflicting messages. Different people have various degrees of tolerance for these conflicting messages.

A passenger inside a ship at sea may see around him just four walls that appear to be stationary, but his body will still feel the motion of the ship. These conflicting signals can lead to motion sickness. A greater rocking motion of the ship will increase the disparity between what the passenger feels and what he sees, and so ships in heavy storms often have many passengers suffering from motion sickness.

An effective way for a person to reduce the likelihood of motion sickness is to look at a stationary point of reference. Ship passengers are commonly advised to get out on the deck and look at a fixed object on land or, if the ship is far out at sea, at the horizon. Thus, as the ship rocks, they can see their own motion relative to a fixed point of reference. If this perceived motion matches the motion they feel, the passengers will avoid motion sickness.

Likewise, a passenger in an automobile can reduce the likelihood of motion sickness by looking out a window at stationary points of reference—buildings, trees, signs, et al. Since the natural tendency for passengers is to look forward, passengers riding in the front seat spend a lot of time looking out the windshield, while rear seat passengers spend much of the time looking at the back of the seat in front of them. Because of this, passengers in the rear seat of an automobile are more likely to suffer from motion sickness than front-seat passengers.

However, this changes when a passenger attempts to read. Many people who have no general problem with motion sickness report that they cannot read in a moving vehicle without getting motion sick, even when they sit in the front seat. It has been suggested that this is because, when a passenger reads, he or she must focus attention on the reading material, and during this time, the passenger will have limited sight of the external environment. A passenger who reads a book, in any seat, gives up his outside view in order to focus on the words on the page, and thus increases the risk that he will get motion sickness.

This same problem may occur for passengers who attempt to watch a movie, use a computer, play a game, write, draw, or engage in any other activity that requires focused attention for extended periods.

The symptoms of motion sickness can include a general feeling of being unwell (malaise), nausea and vomiting, or both, headaches, cold sweating and a pale appearance. Symptoms may alleviate when the motion stops; however, it has been found that for some people it can take a significant period of time for symptoms to subside.

U.S. Pat. No. 6,692,428 to Kania discloses an apparatus having a sensor that detects a motion of an object and a sensory converter which converts the detected motion to corresponding sensory signals, which can be audio, white noise or video. The sensory signals are designed to alleviate motion sickness by using varying audio frequencies and/or colors displayed to the user selected in proportion to the determined motion. In addition, U.S. Pat. No. 6,497,649 to Parker, et al., discloses displaying an independent visual background via a head-mounted display with a visual reference corresponding to the perceptions of a person's vestibular system.

Another attempt to prevent motion sickness is disclosed in U.S. Pat. No. 6,275,998 to Tromble which shows a vision occluding eye shield which completely blocks the peripheral vision of the wearer to the discernment of motion and which blocks most or all of the superior field of vision of the wearer. When worn by a passenger, the device blocks perception of objects passing through the peripheral field of vision in the side windows and through the front window, while allowing the wearer to focus on tasks or objects within the vehicle by looking through the unoccluded portion.

There have also been many attempts to treat motion sickness medically, with pharmaceutical solutions and other medicinal treatments. Some preventative medications can be purchased without a prescription (e.g., Dramamine®, Bonine®, Marezine®). Stronger medicines such as tranquilizers and nervous system depressants usually require a prescription. The downside of using any of these medications includes cost, inconvenience, and potential side effects.

Other medical solutions involve the use of magnetic or metallic bracelets and/or jewelry. Some jewelry is worn on pressure points in an attempt to alleviate motion sickness. It has been found however, that such devices have limited success in preventing motion sickness. As such there exists a need for an effective apparatus, system and method for preventing motion sickness without using medications or medical devices.

The afore-mentioned problems, drawbacks, and disadvantages, in addition to others, are alleviated by the present invention disclosed herein where an object thereof is to provide a non-intrusive, non-medicinal, safe and effective system, method and apparatus for preventing motion sickness while reading text or viewing an image.

SUMMARY OF THE INVENTION

The present invention relates to systems methods and apparatus for allowing a user to view a document in an accelerating environment without becoming motion sick, or with reduced symptoms of motion sickness. The term document is to be construed broadly to include text, graphics, moving images, and other perceptible data adapted for conveying information to a user. In some embodiments, the document includes information marked or printed on a material medium such as paper or polymer film. In other embodiments, the term document refers to a collection of data stored in encoded or un-encoded format for presentation by display on, for example, and electronic or optical screen. By placing such data, whether in fixed material form or in a form reproduced from electronically or otherwise stored data, before a user in the context of an environmental image, the likelihood of a viewer experiencing motion sickness is reduced.

This invention includes a first method for enabling a passenger in a moving vehicle to view a document while preventing or reducing motion sickness. This method includes the steps of 1) printing, writing, drawing, or electronically displaying graphics on a transparent or partially-transparent medium, and 2) positioning the medium so that the passenger can see external, stationary reference points through the medium while viewing the graphics and thus detect his or her own motion relative to those stationary reference points. The graphics may include text and/or images. In some embodiments, the transparent medium is a liquid crystal display or a plastic sheet.

This invention includes a second method for enabling a passenger in a moving vehicle to view a document while preventing or reducing motion sickness. This method includes the steps of 1) mounting a video camera on the vehicle such that the video camera is aimed forward; 2) mounting a monitor in front of the passenger; 3) adjusting the video camera such that its field of view is substantially the same as the passenger's field of view of the monitor; 4) displaying on the monitor live video images transmitted from the video camera; and 5) displaying a document on the monitor, on a medium positioned adjacent to the monitor, or on a transparent medium positioned in front of the monitor such that the passenger can view the document while detecting his or her own motion relative to external stationary reference points in the live video image.

This invention includes an apparatus for enabling a passenger in a moving vehicle to view a document while preventing or reducing motion sickness. This apparatus allows a transparent medium, with a document superimposed, to be positioned in front of the passenger at eye level. In one embodiment, this apparatus includes a transparent board with a tray which can hold a transparent medium, on which a document is displayed. This board is attached by an adjustable arm to a suction cup, which attaches to a window in the vehicle.

In another embodiment, this apparatus is a transparent medium with suction cups which can attach to a window of a vehicle. This medium can display a document. This medium also has a crease or hinge which allows the medium to hang vertically from an inclined window.

In another embodiment, this apparatus is a binder, which includes a set of boards, some of which are transparent, and rings, which hold multiple sheets of transparent media. This binder allows the passenger to position the transparent media at eye level, individually and sequentially, while resting the binder in the occupant's lap. The boards are hinged such that they fold only one way, and can stand erect to support the transparencies.

In another embodiment, this apparatus includes a thin, flexible, transparent medium rolled around a roller which is connected to suction cups, which can be attached to a window. This roller has a spring mechanism that allows the occupant to unroll the transparent medium by pulling it down, and to re-roll the medium by tugging it once more.

This invention includes a first system for enabling an occupant in a moving vehicle to view a document, while preventing or reducing motion sickness. In one embodiment, this system includes a transparent medium, such as an LCD panel, that is capable of displaying dynamic images and a computing device that stores content, such as a map or the pages of a book. The computing device transmits a document to be displayed on the transparent medium. The transparent medium is positioned in front of the occupant such that he or she can see external stationary points of reference through the medium.

In another embodiment, the invention includes a video camera mounted aiming forward out of the vehicle, and a video monitor mounted at eye-level in front of a rear-seat passenger. Live video images are captured and transmitted by the video camera, and are displayed on the monitor substantially simultaneously. A document is displayed—on the monitor along with the live video images, on a medium adjacent to the monitor, or on a transparent medium positioned in front of the monitor—such that the occupant can view the document while seeing the live relative motion of external stationary reference points in the monitor and thus detect his or her own motion.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the Figures, wherein:

FIG. 11 shows a side-window mounted support tray and document according to one embodiment of the invention;

FIG. 12 shows a front-window mounted support tray and document according to one embodiment of the invention;

FIG. 13 shows, in front view, a viewing device according to one embodiment of the invention;

FIG. 14 shows, in side view, a viewing device according to one embodiment of the invention;

FIG. 15 shows, in side view, a viewing device according to another embodiment of the invention;

FIG. 16 shows, in front view, a viewing device according to one embodiment of the invention;

FIG. 17 shows, in side view, a viewing device according to one embodiment of the invention;

FIG. 18 shows, in front view, a viewing device and document according to one embodiment of the invention;

FIG. 19 shows a detail of a hinge according to one embodiment of the invention;

FIG. 20 shows an automobile including an occupant and a viewing device according to another embodiment of the invention;

FIG. 21 shows, in front view, a viewing device and document according to one embodiment of the invention;

FIG. 22 shows, in side view, a viewing device and document in open configuration according to one embodiment of the invention;

FIG. 23 shows, in side view, a viewing device and document in closed configuration according to one embodiment of the invention;

FIG. 24 shows an automobile including an occupant and a viewing device according to one embodiment of the invention;

FIG. 25 shows a hinge arrangement according to one embodiment of the invention;

FIG. 26 shows, in top view, a roller device according to one embodiment of the invention;

FIG. 27 shows, in front perspective view, a roller device according to one embodiment of the invention;

FIG. 28 shows, in side view, a roller device according to one embodiment of the invention;

FIG. 34 shows a display screen including information according to still yet another embodiment of the invention;

FIG. 35 shows a display screen including information according to a further embodiment of the invention;

FIG. 36 shows a display screen including information according to a still further embodiment of the invention;

FIG. 37 shows a display screen including information according to an additional embodiment of the invention;

DETAILED DESCRIPTION

The detailed description set forth below is intended as a description of the presently exemplified motion sickness reduction system, method and apparatus provided in accordance with aspects of the present invention and is not intended to represent the only forms in which the present invention may be prepared or utilized. The description sets forth the features and the steps for preparing and using the motion sickness reduction system, method and apparatus of the present invention. It is to be understood, however, that the same or equivalent functions and components incorporated in the motion sickness reduction system, methods and apparatus may be accomplished by different embodiments that are also intended to be encompassed within the spirit and scope of the invention. Thus while the invention is disclosed and described in the figures with reference to an automobile, those skilled in the art will understand that the invention is equally applicable to other moving environments as well, such as, without limitation, a boat, train, airplane, space craft, and various amusement rides including a roller coaster.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

Figure 1:
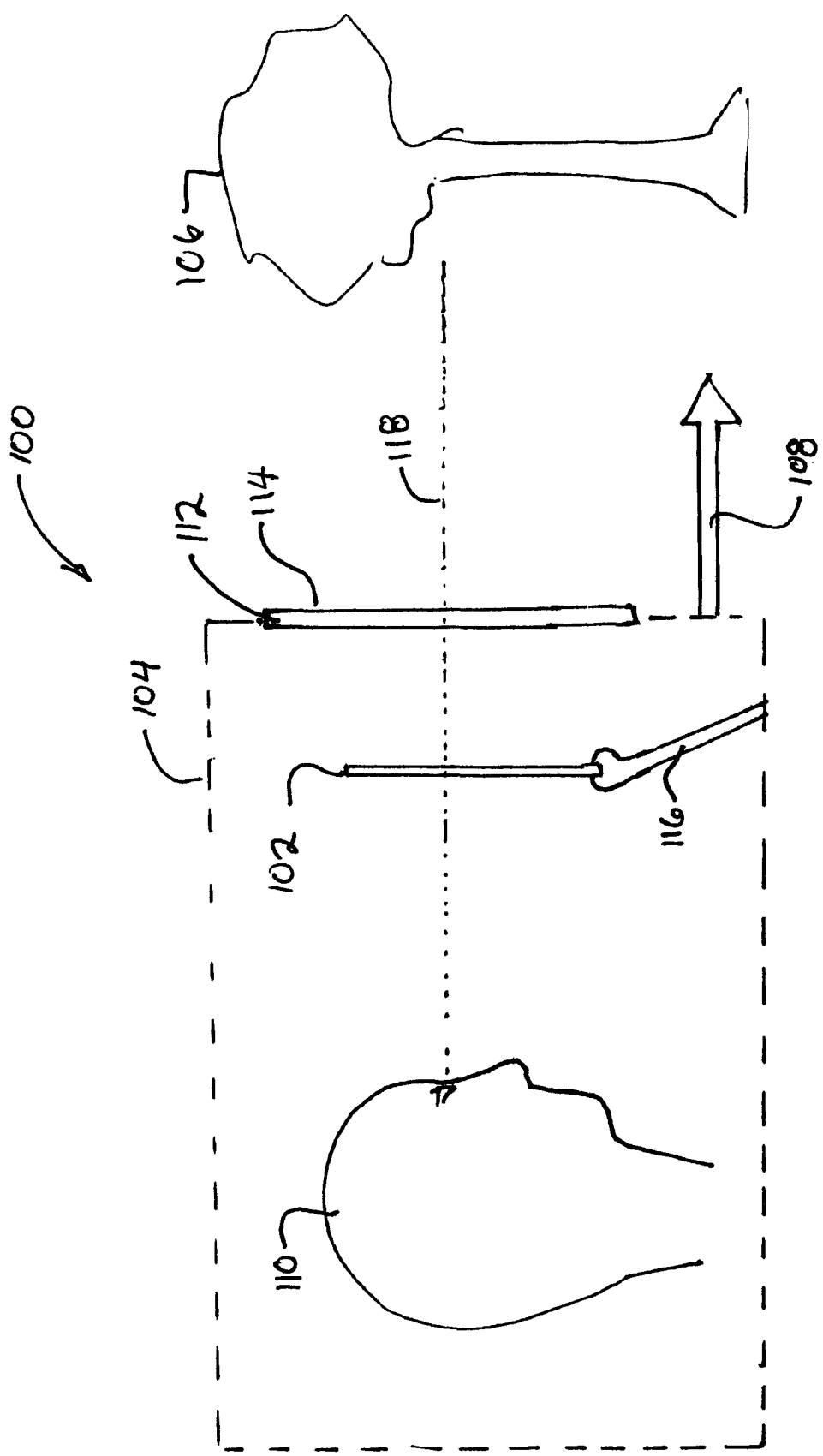
FIG. 1 shows, in schematic form, an apparatus for reading in a vehicle according to one embodiment of the invention.

FIG. 1 shows a motion sickness abatement device 100 according to one embodiment of the invention. The device includes a document presentation device 102 disposed within an apparatus, such as a vehicle 104. The vehicle 104 is adapted to move in relation to an environment thereof, here represented by tree 106. In various embodiments, this relative motion includes at least a first forwardly directed motion 108.

According to one embodiment of the invention, the vehicle 104 is adapted to support an occupant 110 so that a motion of the occupant 110 is substantially coincident with the above-mentioned relative motion 108 of the vehicle 104. The occupant is a user of the motion sickness reduction device according to the invention. In various embodiments, the occupant may be supported within the vehicle on a vehicle seat, in a pendant harness, standingly on a floor of the vehicle, or on a recumbent couch, among other alternatives.

In various embodiments of the invention, the vehicle includes a windshield 112. In at least one embodiment, the windshield 112 is coupled to the vehicle such that at least a portion of an external surface thereof 114 is disposed substantially perpendicular to the direction of motion 108. In the illustrated embodiment, the windshield 112 and document viewing device 102 are shown as separate and discrete devices. In various embodiments however, the functionality of these two devices is integrated into a single apparatus capable of performing both as a windshield and as a document viewing device.

In one embodiment of the invention, as illustrated, the document viewing device 102 is disposed along an optical axis 118 between an eye of the occupant 110 and the external environment 106. In one embodiment of the invention, this optical axis passes through windshield 114.

According to one embodiment, as will be discussed in additional detail below, the document presentation device 102 includes a first light transmissive portion and a second more or less opaque portion. According to one embodiment of the invention, the more or less opaque portion of the document presentation device is configured as text and/or graphics. In one embodiment of the invention, the light transmissive medium is substantially transparent. In another embodiment of the invention, the light transmissive medium is translucent and is adapted to allow the passage of a more or less diffuse optical image impinging inwardly thereon. In still another embodiment of the invention, the light transmissive medium includes a coloring agent adapted to filter, or otherwise color light passing through the medium.

In one embodiment of the invention, a support member 116 is disposed between, and coupled at respective ends to, the document presentation device 102 and the vehicle 104. The support member 116 is configured and adapted to support the document presentation device 102 in an operative orientation between the eyes of the occupant 110 and the forwardly viewed external environment 106. According to one embodiment, the support member 116 includes a pantographic adjustment mechanism. According to another embodiment of the invention, the support member 116 includes a gooseneck style flexible portion. In still another embodiment of the invention, the support member 116 includes one or more rotatably adjustable joints such as disk joints or ball and socket joints. In a still further embodiment of the invention the support member 116 is substantially rigidly fixed between the vehicle 104 and the document presentation device 102.

According to one embodiment of the invention, the document presentation device is suspended from an overhead bearing member of the vehicle by at least one suspending member. In one embodiment of the invention, the suspending member includes a substantially rigid portion. In another embodiment of the invention, the suspending member includes a flexible portion such as a steel cable portion. In still another embodiment of the invention, the suspending member includes an elastic portion such as a coil spring portion, a flat spring portion, or an elastomer portion.

In another embodiment of the invention the document presentation device is supported by a floor or sidewall of the vehicle. In yet another embodiment of the invention, the document presentation device is adapted to be supported in the hands or on the lap of the subject occupant 110 or those of another occupant of the vehicle 104.

In operation, the occupant 110 views text and/or graphics presented on the document presentation device 102 while, substantially simultaneously, viewing the external environment 106. When the vehicle 104 is in motion, this viewing of the external environment 106 is likely to show the relative motion between the external environment image and the text or graphics presented on the document presentation device 102.

In practice, one or the other of the text and/or graphics and the external environment 106 may be in focus at any particular time, while the other is out of focus. Nevertheless, generalized motion of the user 110 with respect to the environment 106 is perceptible to the user even when the environment 106 appears to the user to be less than fully focused.

Without intending to be bound by a particular theory of operation, it is believed that the ability to apprehend the external environment 106 during operation of the apparatus 100 allows the occupant 110 to coordinate visual and other stimuli related to a motion of the vehicle. For example, a typical occupant of a moving, and in particular an accelerating, vehicle will perceive motion/acceleration by the mechanisms of the inner ear, as well as by skin pressure sensations exerted by the floor, seat, or other supporting device.

As noted previously, a perceived inconsistency between these sensory stimuli and perceived visual stimuli is believed to be a causative factor in motion sickness. Therefore, allowing the occupant 110 to so receive external visual stimuli is expected to reduce the risk of motion sickness symptoms.

In addition, by allowing visual perception of the external environment, the occupant 110 is expected to more accurately anticipate accelerative shocks that would otherwise arrive without warning and consequently induce distress.

Figure 2:
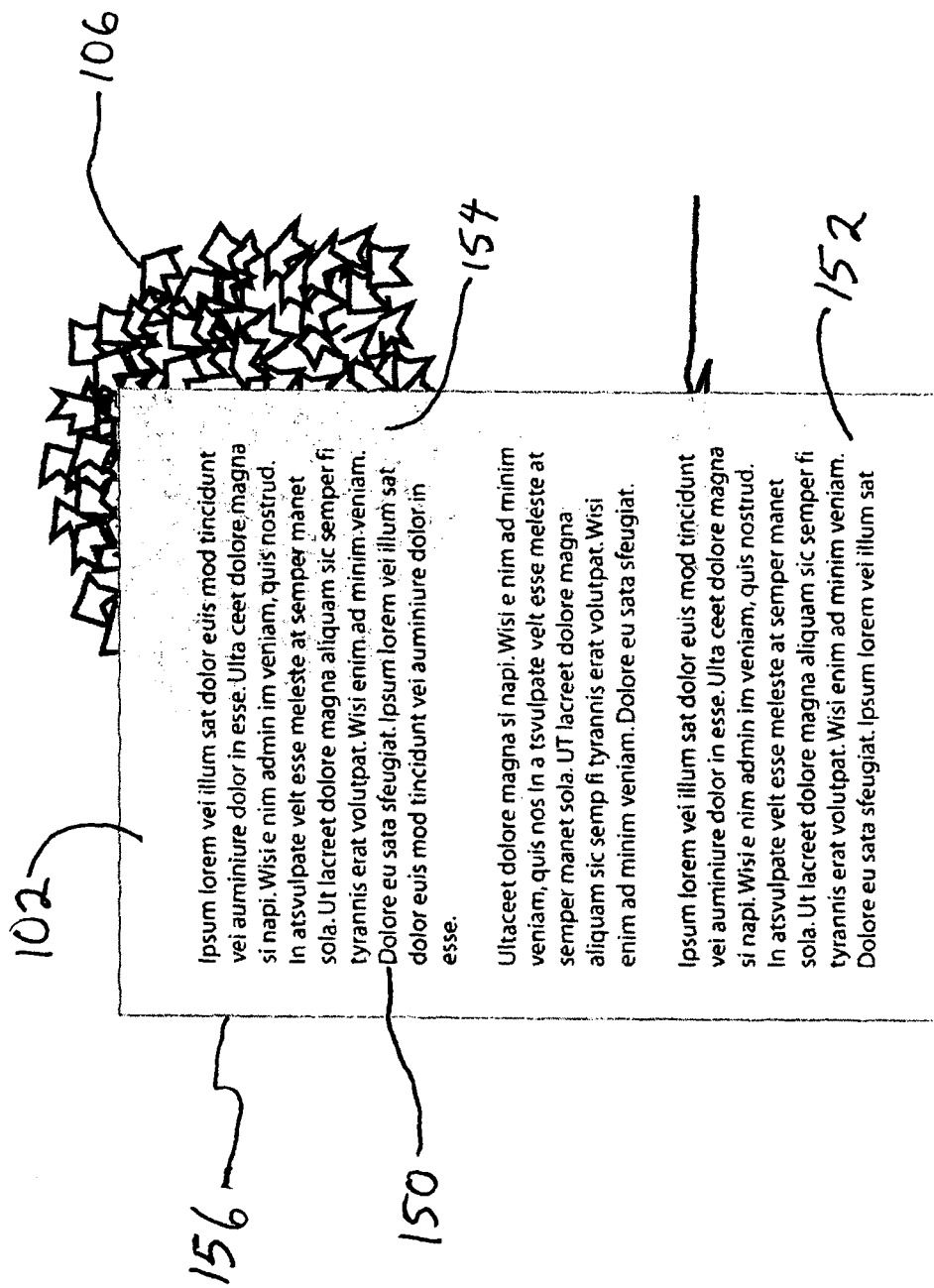
FIG. 2 shows an exemplary view through a display apparatus according to one embodiment of the invention.

FIG. 2 shows an embodiment of the document presentation device 102 in additional detail. In FIG. 2, the document presentation device 102 and external environment 106 are shown as viewed along optical axis 118 (as illustrated in FIG. 1). In one aspect of the invention, a document pattern 150 is shown impressed upon the document presentation device 102. The illustrated document pattern 150 comprises text. One of ordinary skill in the art will appreciate, however, in a wide variety of other information bearing patterns may be used in place of the illustrated text information. For example, in various embodiments, the information pattern may include static and dynamic graphical information such as, for example photographs, animations, videos, game patterns, personal computer desktop display, and other desirable information. In addition, it should be noted that text may be presented in any font and format as is known in the printing and graphical display arts.

In operation, as discussed above, the external environment 106 is visible through the light transmissive medium 152 of the document presentation device 102. In some embodiments, as illustrated, the light transmissive medium slightly obscures the background (as seen for example at 154), improving contrast between the background and the displayed text 150. This makes the text 150 easier to read under some lighting conditions.

As will be discussed in additional detail below, the light transmissive medium 152 may be a static medium, such as a plastic transparency, or may be a dynamic one, such as an LCD panel. In the illustrated embodiment, the light transmissive medium is substantially coextensive with the area of the document presentation device 102. In other embodiments, a bezel or frame is disposed at one or more peripheral edges 156 of the light transmissive medium 152.

In various embodiments, the light transmissive medium 152 may have text 23 or images printed, written, drawn, or electronically displayed. In addition, the document display device may include a combination of statically marked and dynamically variable markings. In one exemplary embodiment, a transparent flexible polymer overlay sheet including one or more substantially opaque markings is disposed over a dynamically patternable electronic display screen. In the case where the text 150 or images are dynamically displayed, such text or images may include text and images from a data set such as an "e-book," or other visual output of a computing device. For example, the images and text may include an output of a video game, whereby a user is enabled to play the video game in a moving vehicle with a reduced risk of experiencing motion sickness. Further examples of printed text or images include, without limitation, books, newspapers, and maps.

Figure 3:
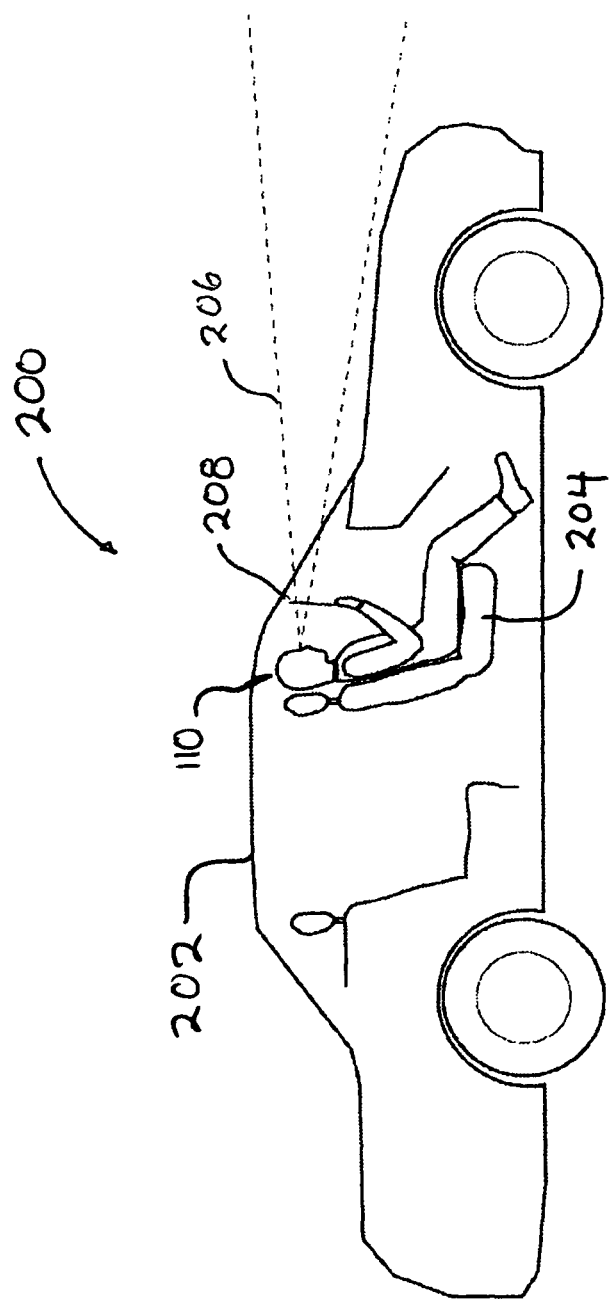
FIG. 3 shows an automobile including an occupant holding a document display device according to one embodiment of the invention.

FIG. 3 shows an additional embodiment 200 of the present invention. In FIG. 3, a document presentation device is disposed within an automobile 202. An occupant 110 of the automobile 202 sits on a seat 204 and holds a document presentation device 208 so that he or she has a view 206 of an external environment through the document presentation device 208.

Figure 4:
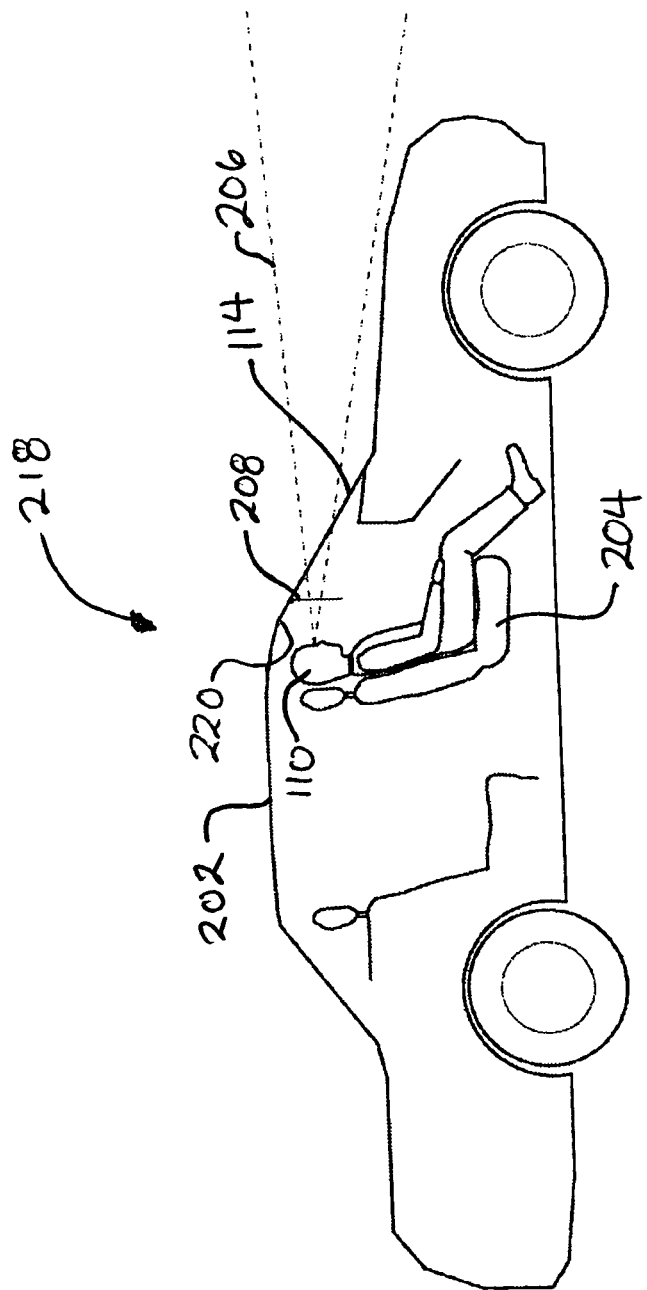
FIG. 4 shows an automobile including an occupant and a display device according to another embodiment of the invention.

FIG. 4 shows a further embodiment 218 of the invention in which a document viewing device 208, similar to that shown in FIG. 3, is directly coupled to an interior surface 220 of an automobile 202. In one embodiment according to FIG. 4 the viewing device 208 is permanently coupled to the interior surface 220 of the automobile 202. In another embodiment, the viewing device 208 is releasably connected to the interior surface 220 of the automobile 202.

In one embodiment, as illustrated, the viewing device 208 is adapted to be coupled to one or more clips conventionally found in an automobile for the support of a sun visor. Advantageously, the viewing device 208 of the FIG. 4 embodiment need not be manually supported, thus avoiding potential fatigue of the occupant 110. It should be noted that in both FIGS. 3 and 4 the occupant 110 is seated in a front seat 204 of the automobile, in proximity to a windshield 114. Accordingly, the occupant 110 has a relatively unobstructed view 206 of the external environment.

Figure 5:
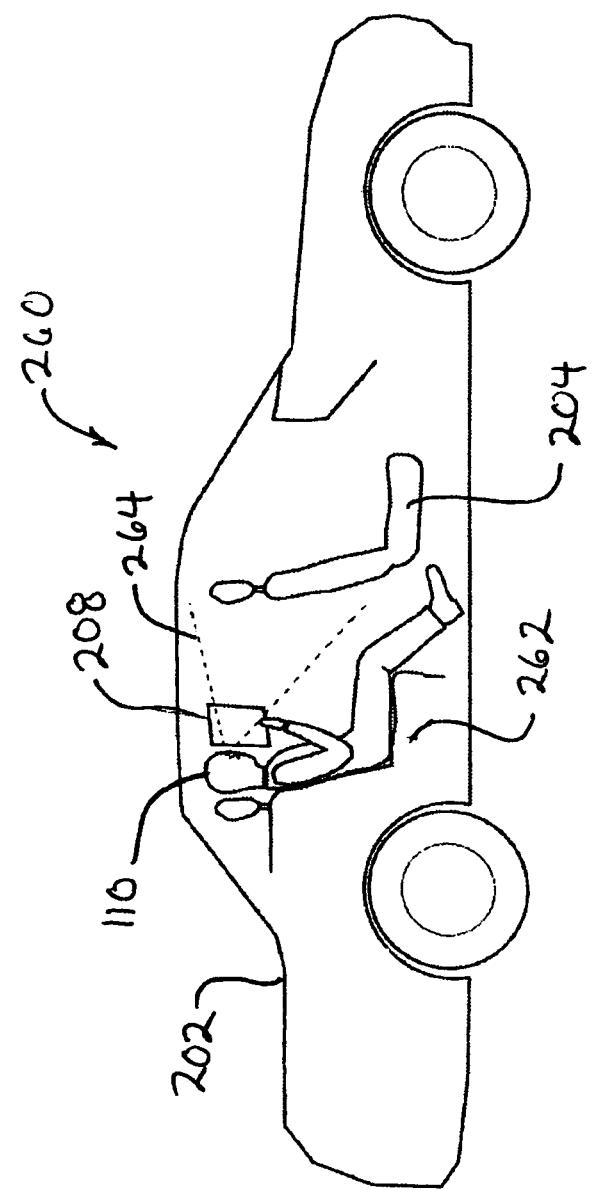
FIG. 5 shows an automobile including an occupant and a display device according to another embodiment of the invention.

FIG. 5 shows a further embodiment 260 of the invention in which an occupant 110 is seated in a rear seat 262 of an automobile 202. In the illustrated embodiment, the occupant 110 is shown manually supporting a viewing device 208. Depending on the seating position of the occupant 110, the occupant's view 264 of the external environment may be out the side window or out the front windshield.

Figure 6:
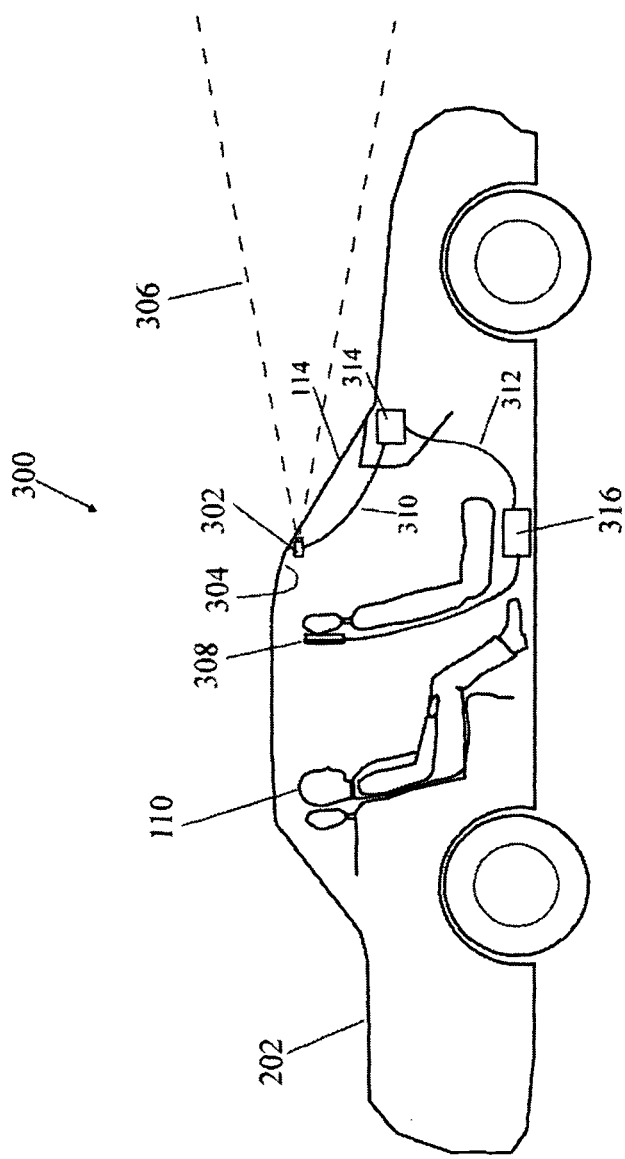
FIG. 6 shows an automobile including an occupant and a display device according to another embodiment of the invention.

In FIG. 6, an embodiment 300 is illustrated in which an occupant 110 in a rear seat receives information related to the external environment by way of, for example, a video camera 302. In the illustrated embodiment, the video camera is supported by an internal surface 304 of the automobile 202 and is disposed so as to have a clear view 306 of an external environment in which the automobile 202 is operating.

In the illustrated embodiment, an image captured by the video camera 302 is converted to an electronic signal and transmitted to a document presentation device 308 by way of one or more electronic signal cables 310, 312. In various embodiments, the electronic signal is a digital signal, an analog signal, or a hybrid signal combining both digital and analog aspects. In a further embodiment of the invention, the signal is an optical signal, and the signal cables 310, 312 are, correspondingly, optical fiber conductors.

In one embodiment of the invention, as illustrated, a signal mixer device 314 and/or a signal amplifier device 316 is disposed along the signal path between the video camera 302 and the document presentation device 308. The signal mixer device serves to combine an image signal received from the video camera 302 with a text/graphics signal to produce a compound signal. The compound signal, when received at the document presentation device 308 is adapted to cause the document presentation device 308 display a compound image including a textural/graphical image superimposed over an image of the external environment.

The signal amplifier device 316 is adapted to receive a signal and increase its amplitude while transmitting an amplified signal to the document presentation device. According to a particular embodiment, the amplifier 316 may be an intermediate frequency or radio frequency linear amplifier, as is known in the art.

Advantageously, the embodiment 300 shown in FIG. 6 allows an occupant 110 seated in a rear seat of an automobile 202, or other vehicle, to enjoy the benefits of the present invention without having direct visual access to a windshield 114 or other external window.

Figure 7:
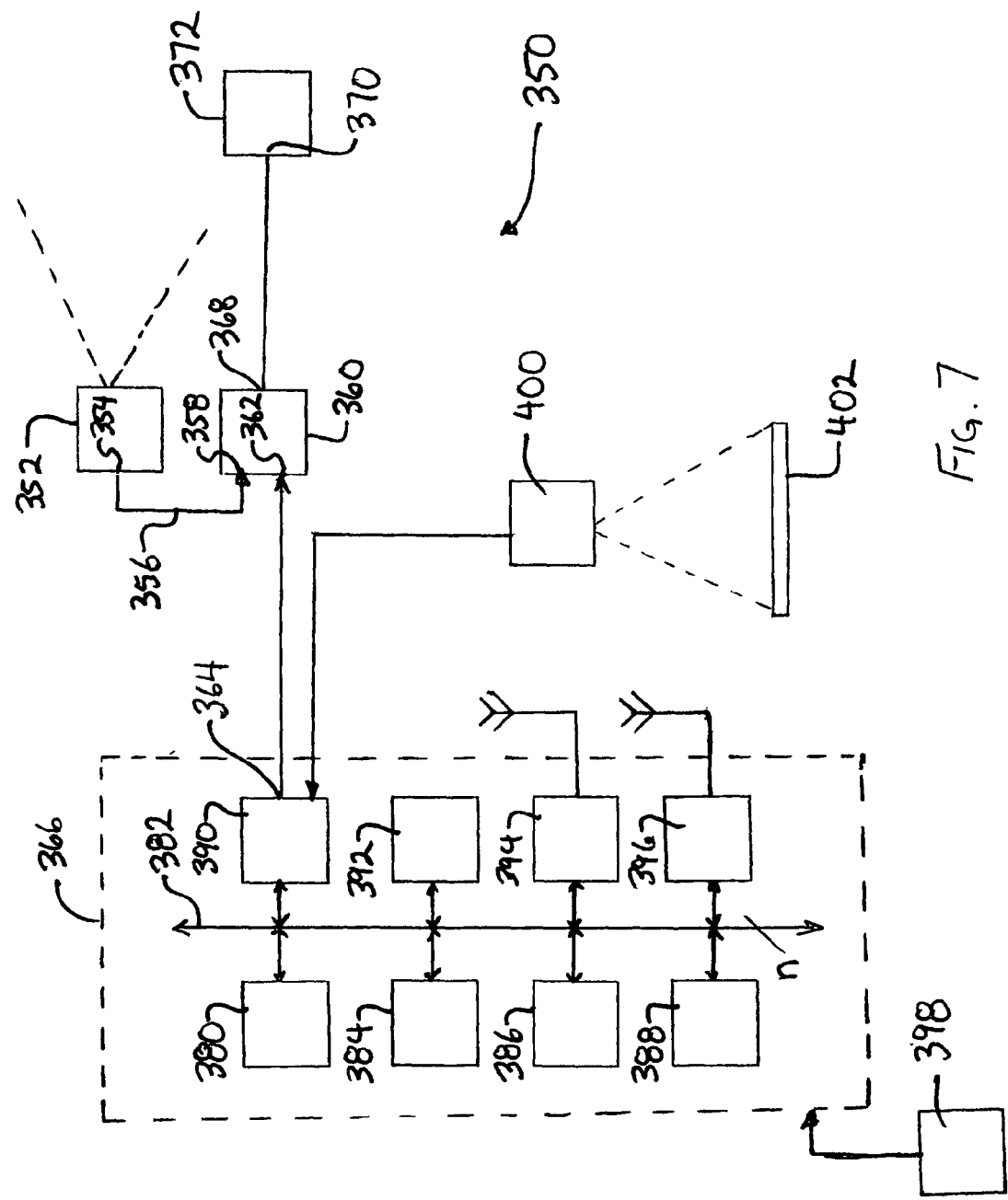
FIG. 7 shows, in block diagram form, a document display system according to one embodiment of the invention.

FIG. 7 shows, in additional detail, a further embodiment 350 of the invention including a video camera and a digital computer. In the illustrated embodiment, a video camera 352 captures an optical image of an external environment of a vehicle. The camera 352 converts the optical image into, for example, an electronic signal which is output from an output port 354 of the camera 352 and conveyed by a signal cable 356 to a first input port 358 of a signal mixer device 360. A document image signal is received at a second input port 362 from an output port 364 of a digital computer device 366. A mixed signal is transmitted from a further output port 368 of the signal mixer device 360 to an input 370 of a document presentation device 372.

According to one embodiment of the invention, as illustrated, the computer device 366 includes a central processing unit 380. The central processing unit 380 is coupled to a signal bus 382. In various embodiments, the signal bus 382 includes a data bus, an address bus and a control bus.

Also coupled to the signal bus is a random-access memory device 384, a read-only memory device 386, and a further memory device 388 such as a (magnetic) hard disk drive. In another aspect of the illustrated embodiment, the computer device 366 includes an input/output (I/O) port 390 and a removable storage medium device 392 such as, for example, a CD-ROM drive, DVD-ROM drive, flash memory adapter, or other memory device such as is known of the art, or may become available.

In the illustrated embodiment, the computer device 366 also includes a communication device 394 such as, for example, a wireless network adapter device. The communication device 394 is coupled to the signal bus 382. Also included in the illustrated embodiment, and coupled to the signal bus 382, is a global positioning system (GPS) adapter 396. A power supply 398 is coupled to the computer system 366 to provide power to its various components and subsystems.

In the illustrated embodiment 350, the I/O port 390 is coupled to the signal mixer device 360 and is also signalingly coupled to a document imaging device 400. The document imaging devices adapted to acquire an image of a document 402. In one embodiment of the invention, the document imaging device 400 is a still camera. In another embodiment of the invention, the document imaging device 400 is an optical scanner device. One of skill in the art will appreciate that the document imaging device is, in various embodiments, continuously connected to the computer device 366 for real-time acquisition of document images. In other embodiments of the invention, the document imaging device 400 is connected to the computer device 366 intermittently. During intervals of connection, document images acquired by document imaging device 400 are stored in a memory device of the computer device 366 such as, for example, hard disk drive 388. Thereafter, the document imaging device 400 is disconnected from the computer device 366 and document image signals recovered from the hard disk drive 388 are transmitted from the computer device 366 to the signal mixer device 360.

One of skill in the art will appreciate that the embodiment 350 shown in FIG. 7 is only one of many embodiments that may be employed to effect the desired motion sickness reduction. For example, the mixing of environmental image signals and document image signals may be performed within the computer device 366, rather than in an external signal mixer 360. The present invention is intended to encompass all such embodiments, limited only by the scope of the claims appended hereto.

Figure 8:
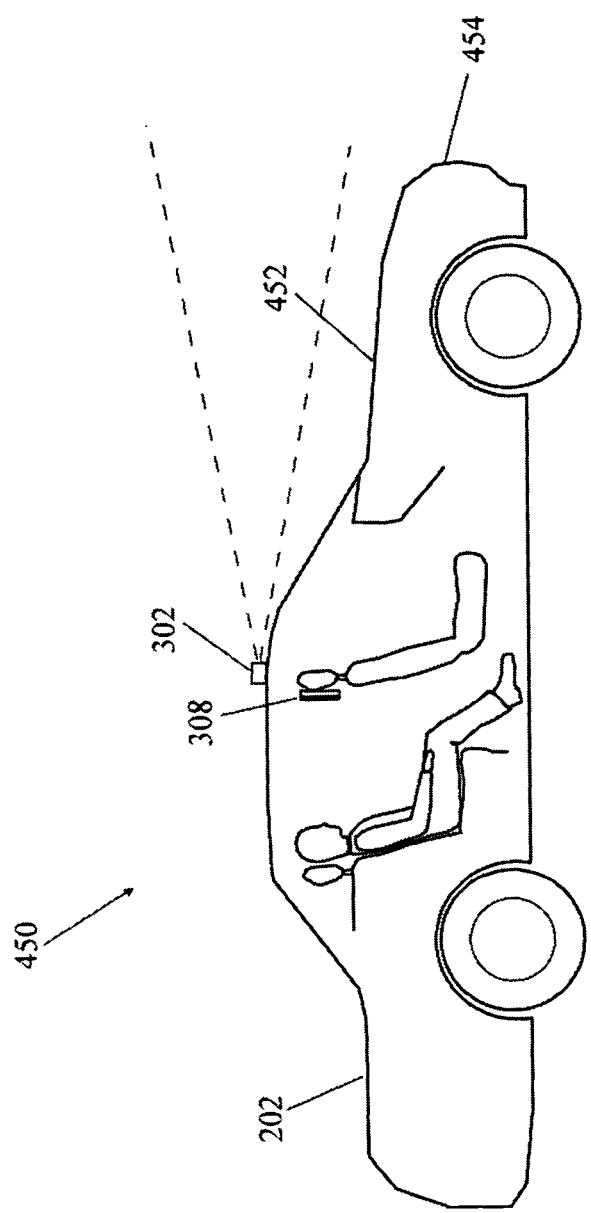
FIG. 8 shows an automobile including an occupant and a display device according to another embodiment of the invention.

FIG. 8 shows a further embodiment 450 of the invention. Like the embodiment 300 shown in FIG. 6, embodiment 450 includes a video camera 302 and a document presentation device 308 for presentation of an image to an occupant 110.

In embodiment 300 of FIG. 6, video camera 302 is mounted within the automobile 202 and receives an image of the environment through windshield 114. In contrast, embodiment 450, as shown in FIG. 8, includes video camera 302 mounted externally to the automobile 202. One of skill in the art will appreciate that a video camera 302 may be mounted in a wide variety of locations such as, for example, on a hood 452, or behind a grill 454, of automobile 202, and each of these arrangements is considered to be within the scope of the invention.

Figure 9:
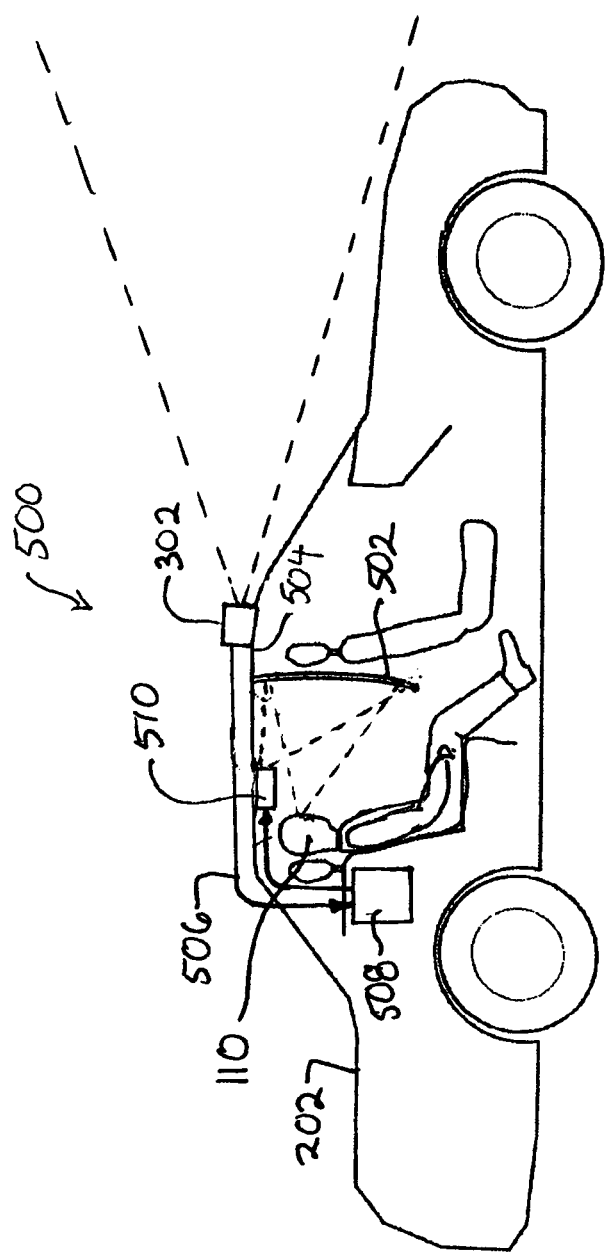
FIG. 9 shows an automobile including an occupant and a display device with a projection screen according to another embodiment of the invention.

FIG. 9 shows a further embodiment 500 of the invention. In the illustrated embodiment, a projection screen 502 is coupled to, and supported by, an internal surface 504 of automobile 202. A video camera 302 is supported by the automobile 202 and is oriented to capture a moving optical image of an environment of the automobile. The moving optical image is converted by the camera 302 into an image signal which is conveyed by a signal conductor 506 to a computer device 508.

One of skill in the art will appreciate that the present representation is schematic in nature. Accordingly, the illustrated locations of various components including, for example, signal conductor 506 are selected for illustrative convenience. Other locations for these components are to be chosen according to the requirements of a particular application, and all such locations and arrangements are considered to be within the scope of the invention. In addition, the use of communication cables is optional, and in various embodiments, wireless communications, such as radio-frequency communications, microwave communications, and optical communications are employed concurrently with, or in place of, such cables.

The computer device 508 combines the environmental image signal, received by way of conductor 506, with a document image signal produced, for example, from data stored within the computer device 508 to produce an output image signal. The output image signal is conveyed from the computer device 508 to a projection camera 510. The projection camera 510 receives the output image signal and projects a further optical image onto a projection screen 502. Accordingly, the automobile occupant 110 is able to comfortably view a combined image reflected by the projection screen 502. The combined image includes a document image superimposed on an image of the external environment of the automobile 202. A particular advantage of embodiment 500 is that one or more occupants of the automobile 202 may simultaneously perceive and benefit from the image projected on the projection screen 502.

Figure 10:
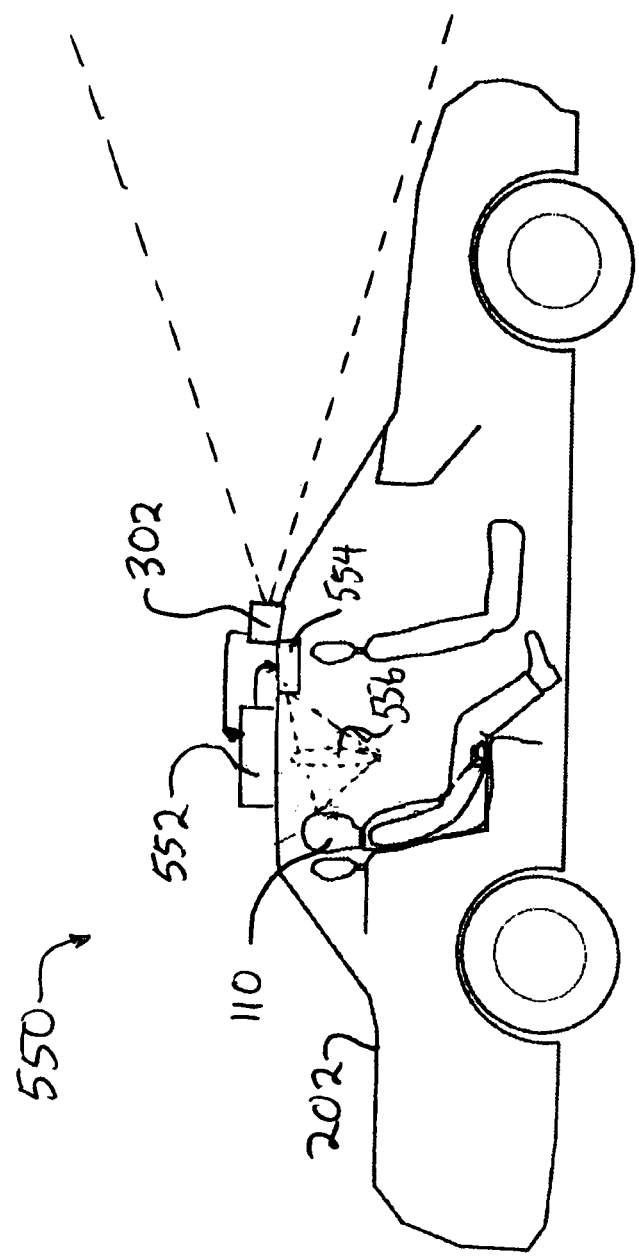
FIG. 10 shows an automobile including an occupant and a display device with a holographic projector according to another embodiment of the invention.

FIG. 10 shows a further embodiment 550 in which an environmental image signal is received at a computer device 552 from a video camera 302. An output signal from the computer device 552, including environmental image and document image data, is received at a holographic projection device 554.

In operation, the holographic projection device 554 produces a holographic image 556 at a spatial region within an automobile 220 such that the holographic image 556 is readily perceptible to an occupant 110 of the vehicle 202. As in some other embodiments of the invention, the holographic image 556 includes an environmental image portion and a document image portion, whereby the occupant 110 may read the document image portion, while the automobile 202 is in motion, without experiencing motion sickness.

FIG. 11 shows a further embodiment 570 of the invention. As illustrated, a light transmissive support tray 572 is adapted to receive a document 574 printed on a substantially transparent material 576. For example, the material 576 may include mylar, vinyl or other polymer material, glass, or any other appropriate transparent medium. The light transmissive support tray may include translucent and/or transparent regions.

It is worth noting that the view of the external environment need not, in every circumstance, be taken forwardly. Rather, in various embodiments and applications, a user may be facing in any direction. Accordingly, in the presently illustrated embodiment, a coupling including a shaft 578 and an adhesive disk 580 are adapted to support the light transmissive support tray 572 in substantially fixed spatial relation to a side window of an automobile. In one illustrative embodiment of the invention, the adhesive disk includes an atmospheric suction cup. Accordingly, an occupant 110 is able to read the documents 574 while sitting in a front or rear seat of the automobile and looking outwardly through a side window thereof.

FIG. 12 shows an additional embodiment 590 of the invention. In FIG. 12, a suction cup 592 is coupled to an internal surface 594 of an automobile windshield 596. In the illustrated embodiment, an adjustable arm 598 connects a transparent board 600 to the suction cup 592. A tray 602 is formed at a lower edge of the transparent board 600. The tray 602 supports a transparent medium 604. An occupant 110 of an automobile can view text disposed on the transparent medium 604 while looking through both the transparent medium 604 and the transparent board 600.

FIG. 13 shows an additional embodiment of the invention 620. In FIG. 13, three suction cups 622 attach a transparent medium 604 to a window. An image of a map 628 is displayed on the transparent medium 604. A stationary reference point 626 is behind the transparent medium 604, and is visible through it. A crease or hinge 624 in the transparent medium 604 allows the transparent medium 604 to hinge when necessary. FIGS. 14 and 15 show side views of the FIG. 13 embodiment in various applications. In FIG. 14, the suction cups 622 are shown attached to a substantially vertical window such as a side window of an automobile.

In FIG. 15, the suction cups 622 are shown coupled to a windshield 640 which sits at an oblique angle with respect to a vertical orientation. A crease 642 in the transparent medium 604 allows the transparent medium 604 to maintain a substantially vertical orientation. A lower edge of the transparent medium 604 includes a weight 644. The weight 644 is adapted to prevent the lower edge of the transparent medium 604 from curling upwardly while in use.

FIG. 16 shows a front view of an additional embodiment of the invention. The FIG. 16 embodiment includes an apparatus which allows a user to position a transparent medium at eye level by resting the apparatus on his or her lap. The embodiment of FIG. 16 includes a transparent board 680 with a shelf 682 disposed at one end thereof.

FIG. 17 shows a side view of the embodiment of FIG. 16. In FIG. 17 it is clear that the shelf 682 projects outwardly from the transparent board 680.

In FIG. 18 a support board 686 is coupled to the shelf 682 by a hinge 684.

FIG. 19 shows the hinge 684 of the FIG. 18 embodiment in additional detail. The board 686 and the hinge 684 are structured such that the board 686 does not open more than about 180 degrees relative to the transparent board 680.

Referring again to FIG. 18, one sees that shelf 682 is adapted to receive a transparent medium 604. The transparency of the transparent board 680 allows a user to view an external environment through the board 680 and transparent medium 604. This arrangement is seen more clearly in FIG. 20 in which an occupant 702 in a vehicle 704 holds the apparatus 706 on his or her lap, and has a view 708 through the apparatus 706 of the external environment.

FIG. 21 shows, in front view, an additional embodiment 720 of the invention including an apparatus adapted to support one or more sheets of transparent media 722. Use of the apparatus enables a user to readily position the transparent sheets at eye level one at a time. In use, the apparatus is supported, for example, on the lap of a user. The apparatus includes several parts which stand erect when open, and which close to wrap around and protect the transparent media.

FIG. 22 shows the apparatus of FIG. 21 in side view. As shown in FIG. 22, the apparatus is in open configuration, and ready for use. FIG. 23, also in side view, shows the apparatus closed for protection and storage of sheets of transparent media 722. As shown in FIGS. 21-23, a first transparent board 724 is coupled to a second transparent board 726. Second transparent board 726 is, in turn, coupled to a third board 728. Third board 728 is coupled to a flexible base 730 and flexible base 730 is coupled to a further board 732.

In the illustrated embodiment, two rings 734 are disposed within respective holes in board 732 and in transparent media 722. The rings 734 are adapted to support transparent media 722, which may be disposed alternatively behind and in front of the board 732. In addition, a single sheet 740 of transparent media 722 is operatively disposed above board 732 and against the transparent board 724. This arrangement allows a user to read a set of transparent media one page at a time, for example.

FIG. 24 shows an occupant 760 sitting in a front seat of a vehicle 762 and holding the apparatus of FIGS. 21-23 in his lap. According to this embodiment, the occupant is able to look through the apparatus at an external environment of the vehicle 762.

FIG. 25 schematically shows a cross-section of the hinged connections between three parts of the apparatus of FIGS. 21-24. The transparent board 724 is connected by a hinge 764 to the transparent board 726, which is connected by a hinge 766 to the board 728. The hinge 764 and the hinge 766 are on the same side of the set of boards. This allows the boards to fold only one way, and to stand erect when needed.

FIGS. 26-28 show an additional embodiment of the invention. FIG. 26 shows this further embodiment in top view while FIG. 27 shows the front view in FIG. 28 shows the side-view. In FIG. 27 a transparent medium 780 is coupled to a spring coil roller 782. An image of a map 784 is printed on a transparent medium 780. In other embodiments, text or other graphics are printed on the transparent medium 780. There is a pull tab 786 and a weight 788 attached to the bottom of transparent medium 780. When the transparent medium is extended, a user may view an external environment through the transparent medium while concurrently reading the map, text or other graphics.

In FIG. 27, the spring coil roller 782 is attached to a connecting bar 790, on which are attached two suction cups 792. The suction cups 792 can be attached to a window.

Figure 29:
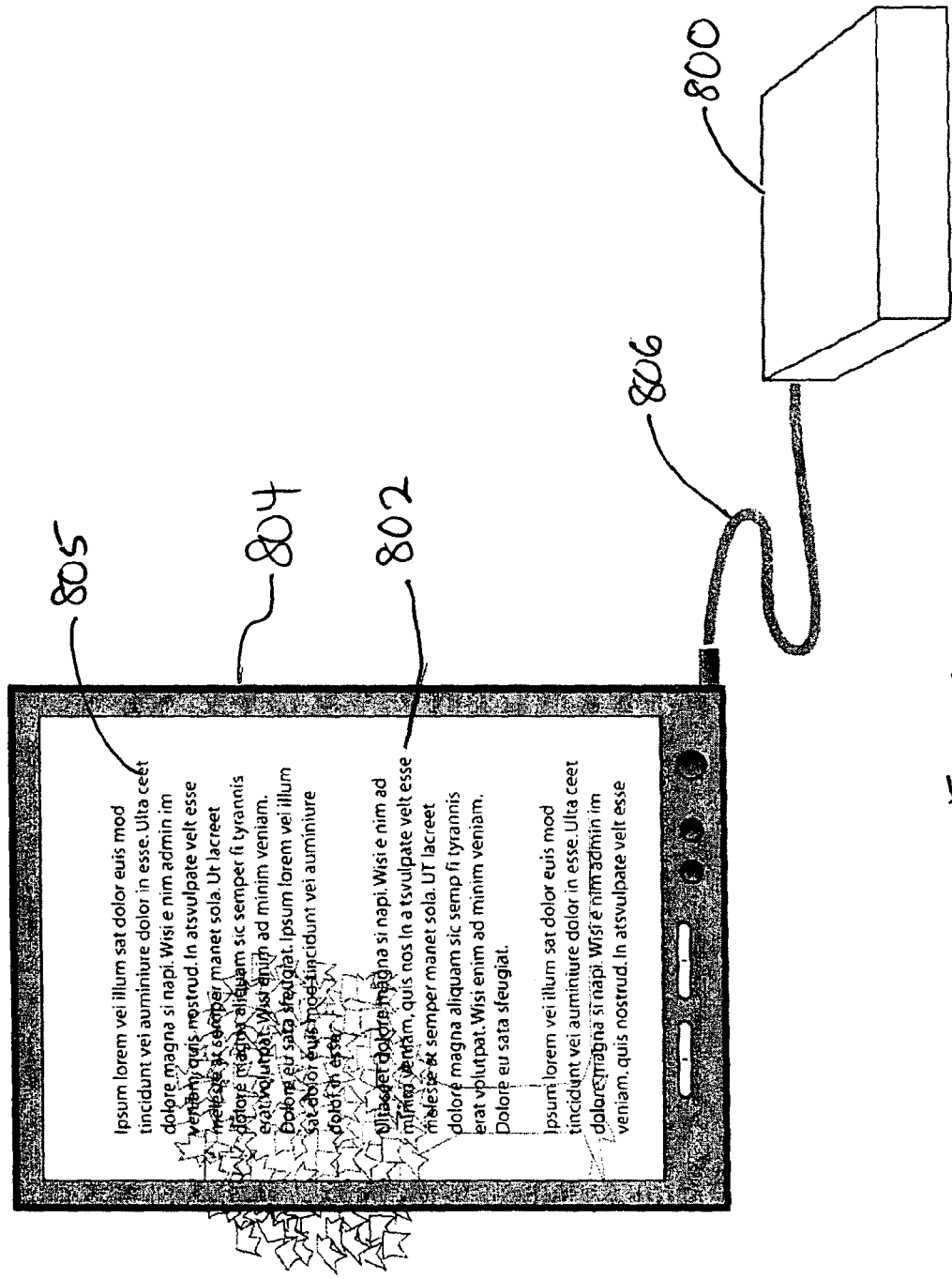
FIG. 29 shows an electronic display according to one embodiment of the invention.

FIG. 29 shows a further embodiment of the invention including a computing device 800 which transmits a video image 802, representing, for example, a page of text 805 of an e-book, to a transparent LCD panel 804 via a cable 806. In some embodiments, the video image is transmitted wirelessly. In other embodiments, the computing device is integrated into the transparent LCD panel. An external environment is visible through the LCD panel 804. As will be readily understood, the transparent LCD panel 804 may be mounted in a vehicle.

Figure 30:
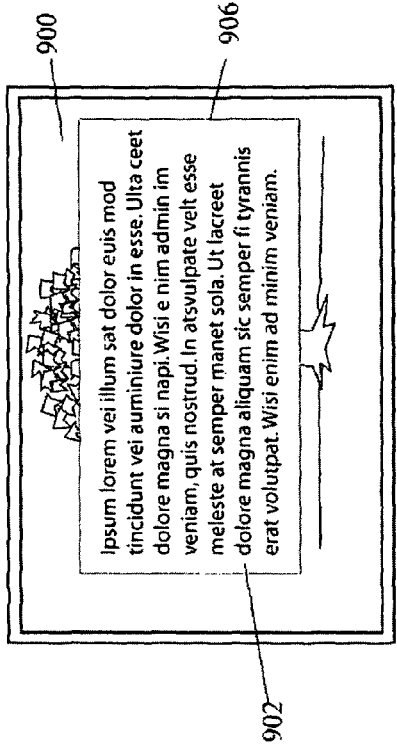
FIG. 30 shows a display screen including information according to one embodiment of the invention.

FIG. 30 shows an exemplary display of a video image 802 on a display screen.

Figure 32:
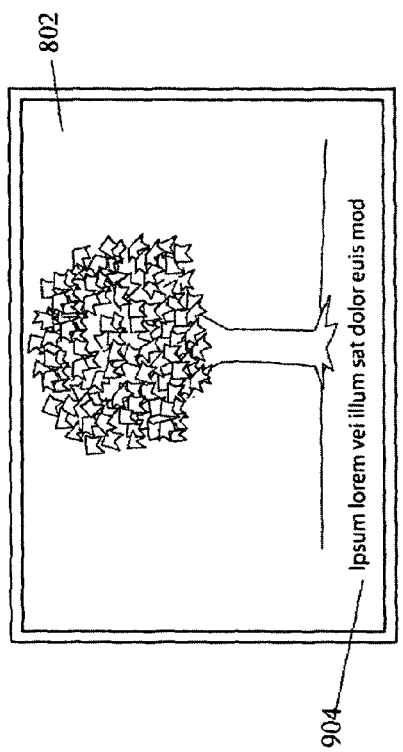
FIG. 32 shows a display screen including information according to still another embodiment of the invention.
Figure 31:
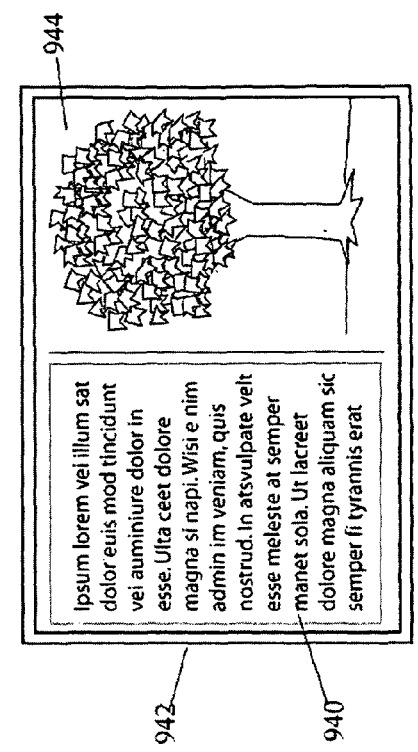
FIG. 31 shows a display screen including information according to another embodiment of the invention.
Figure 33:
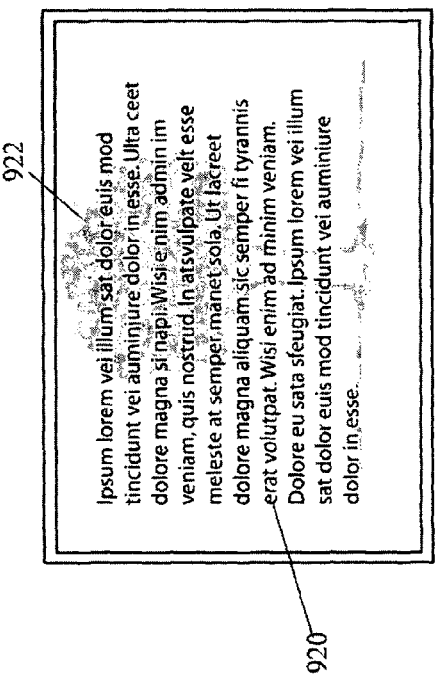
FIG. 33 shows a display screen including information according to yet another embodiment of the invention.

FIGS. 31-33 show various other exemplary display screens including, for example, a live video image 900 along with text 902.

FIG. 30 shows text 904 displayed as a subtitle. In some embodiments, the text 904 scrolls across the bottom of the screen.

FIG. 31 shows the text 902 in an opaque graphical box 906 superimposed over a video image 900 such that only portions of the video image 900 are visible.

FIG. 32 shows the text 920 superimposed on a video image 922 such that the video image 922 is visible through the text.

FIG. 33 shows text 940 positioned in a subset of the means of display 942, adjacent to a video image 944.

FIGS. 34-37 show various embodiments of a document display device according to the invention.

FIG. 34 shows a video image 960 being displayed in a limited region of display 962, such as, for example, in a software window on a computer desktop.

FIG. 35 shows the video image 970 positioned next to a video image 972 of a motion picture, such as might be transmitted by a computing device such as a DVD player.

FIG. 36 shows the video image 974 positioned next to the image of a map 976, and FIG. 37 shows the video image 980 positioned next to a display 982 of a video conference call.

Figure 38:
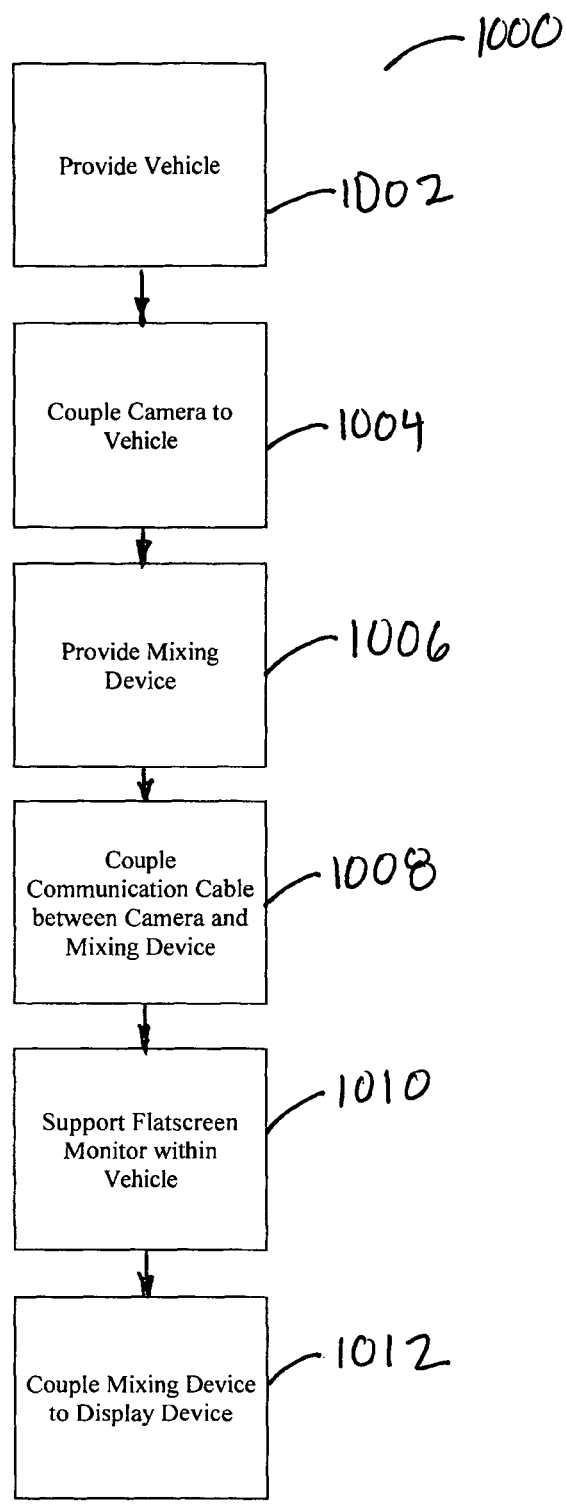
FIG. 38 shows, in block diagram form, a method of manufacturing a motion sickness reduction device according to one embodiment of the invention.

FIG. 38 shows, in block diagram form, a method of manufacturing a motion sickness reduction device 1000. The method 1000 includes providing 1002 a vehicle or other support likely to undergo repeated acceleration, and coupling 1004 an image acquisition device such as a video camera to the vehicle or other support. This coupling step may include substantially rigidly coupling the camera directly to the vehicle. In other embodiments, this coupling step may include providing a stabilizing device such as a passive or active shock absorber between the vehicle and the camera.

The method also includes providing 1006 a mixing device, such as a digital computer or analog mixer. In one embodiment, the mixing device is substantially fixedly mounted to the vehicle. In one embodiment, an electronic communication cable is provided 1008 between the camera and the mixing device. In another embodiment, and optical communication cable is provided between the camera and mixing device. In still another embodiment of the invention, the camera and mixing device are adapted to communicate wirelessly with one another.

In one embodiment of the invention, a display device such as a flatscreen monitor is supported 1010 within the vehicle. According to one embodiment of the invention, the mixing device is signalingly coupled 1012 to the display device. This coupling 1012 between the mixing device and the monitor, according to one embodiment, includes connecting a signal cable between the mixing device and the monitor. In another embodiment of the invention, coupling 1012 is accomplished by providing wireless communication equipment coupled respectively to the mixing device and the monitor. In the described arrangement, the monitor is adapted to display an image including an image received by the video camera and a further image including, for example, a text document image, a graphical image, a videogame image, or some other image in such a fashion that the reader can read the further image without becoming motion sick as the vehicle is repeatedly accelerated.

Figure 39:
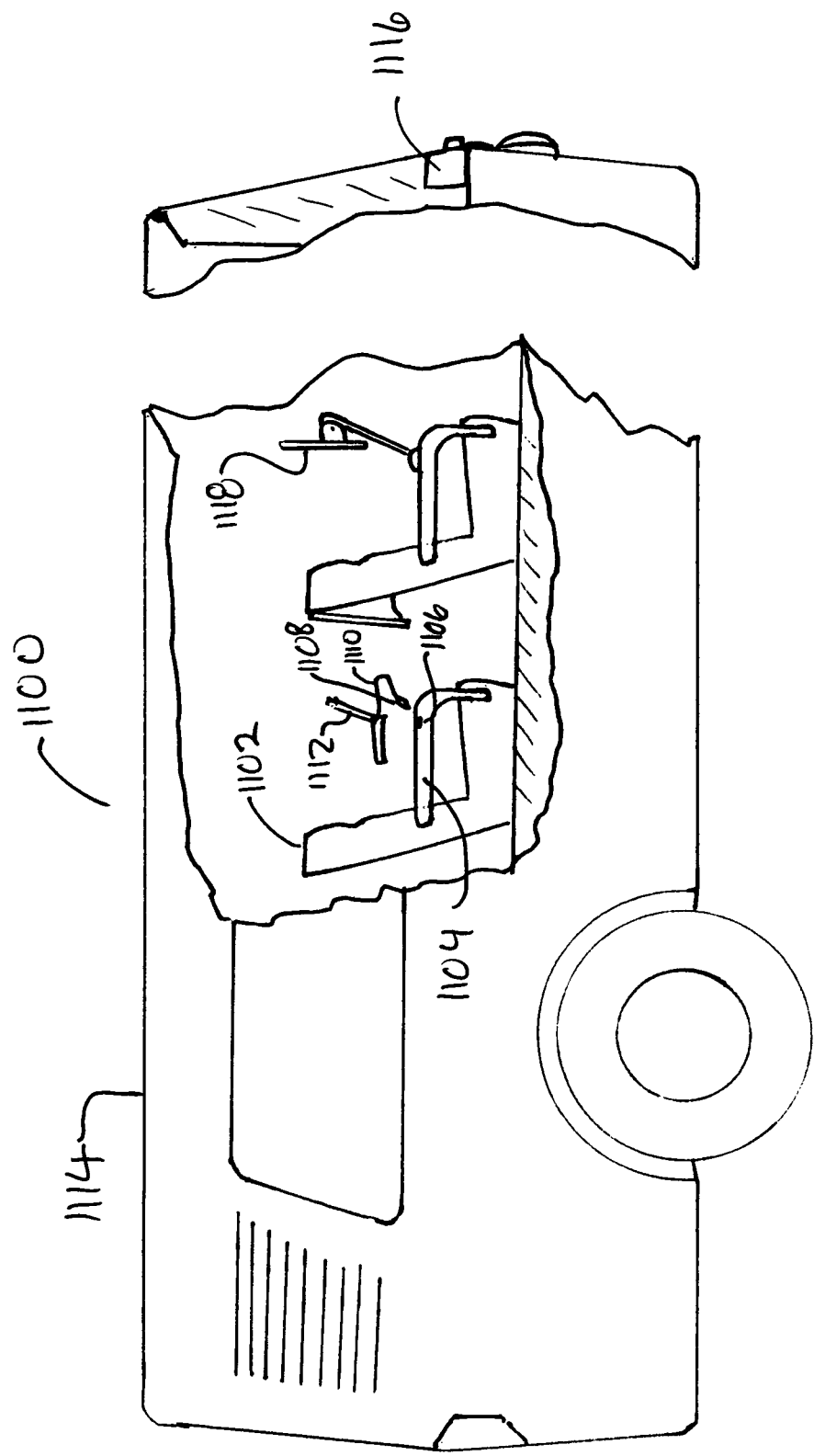
FIG. 39 shows, in schematic cutaway form, a motion sickness abatement device according to one embodiment of the invention.

FIG. 39 shows a further embodiment 1100 of the invention. In embodiment 1100, a passenger in a vehicle 1114 is provided with a seat 1102 having, for example, an armrest 1104 or other supporting member. The armrest 1104 includes a signal coupling device such as, for example, an electronic coupling receptacle or an optical data coupling receptacle.

Where the signal coupling device is a signal coupling receptacle, the receptacle is adapted to receive a corresponding signal coupling plug 1108. The signal coupling plug 1108 is connected to an appropriate signal cable 1110, which is, in turn, connected to a display device 1112 such as, for example, a laptop computer, an electronic book (e-book), a personal digital assistant (PDA), or other device adapted for the display of written or graphical material and capable of displaying environmental images.

In one embodiment of the invention, the vehicle 1114 is a multi-passenger vehicle such as a bus, a train, a limousine, an airplane, or other vehicle. In one embodiment of the invention, a single camera 1116 is supported by the vehicle and is adapted to receive a dynamic environmental image from a direction forwardly of the vehicle. In one embodiment of the invention, a single camera 1116 generates a video image signal that is displayed on multiple screens 1112, 1118.

Figure 40:
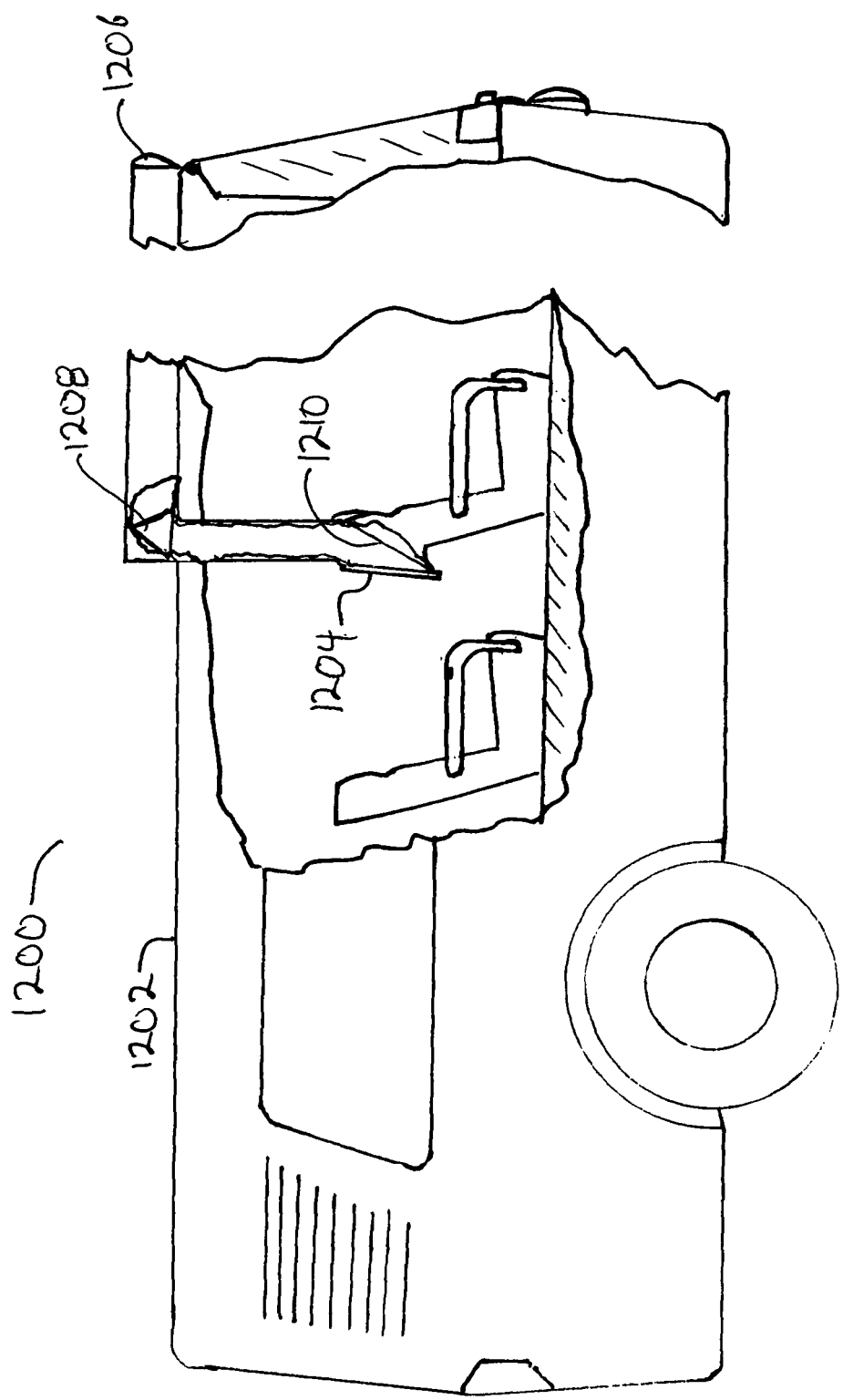
FIG. 40 shows, in schematic cutaway form, a motion sickness abatement device according to another embodiment of the invention.

FIG. 40 shows another embodiment 1200 of the invention in which an optical display device is mounted on a mobile conveyance 1202 of such as an automobile. The optical display device captures light from outside of the mobile conveyance 1202 and transfers that light, by optical means, to a display screen 1204 within the conveyance. In one embodiment of the invention, this transfer of light is accomplished by means of an optical waveguide such as, for example, a graded or un-graded optical fiber. In another embodiment of the invention, the light transfer is accomplished by means of one or more of a lens 1206, a prism 1208, and a mirror 1210.

In one embodiment of the invention, the display screen 1204 is mounted for viewing by one or more passengers within the conveyance. In another embodiment of the invention, the display screen is mounted for viewing by a single passenger.

According to one embodiment of the invention, the optical display device is a periscope adapted to collect light from outside the vehicle and transfer that light to the viewing passenger. In one embodiment of the invention, the periscope collects light by way of an aperture disposed above the viewing passenger. In another embodiment of the invention, the periscope collects light by way of an aperture disposed forwardly of the passenger. In still another embodiment, the periscope collects light by way of an aperture disposed to one side or another of the viewing passenger.

In another embodiment, the invention, includes a method of doing business including receiving a consideration for providing access to an anti-motion sickness device, or providing a signal to assist in motion sickness prevention. In one embodiment, the invention includes providing an image of a relatively moving environment to a passenger in a vehicle. For example, in one embodiment, the invention includes providing a video signal receive from a camera mounted to receive an image from forwardly of the moving vehicle.

The video signal is provided to a signal coupling, such as an electronic coupling. The electronic coupling is adapted to be coupled, by way of a signal-conveying cable, to a display device such as, for example, a laptop computer, an electronic book, a personal digital assistant, or other display device. In one embodiment of the invention, the business includes providing a digital memory medium including software. The software is adapted to display a document image superimposed on a moving image corresponding to the video signal.

In one embodiment of the invention, the document image is derived from data stored within the laptop, e-book, PDA, etc. In another embodiment of the invention, document data is supplied by a memory device to a device permanently mounted to the vehicle and adapted to superimpose the document image on the video signal image. In one embodiment of the invention, the laptop computer, or other display device, is provided by the customer, or a third party.

While the foregoing embodiments have been largely described in relation to vehicular applications, one of skill in the art will appreciate that the scope of the invention is broader. In its various embodiments the present invention will find application in a wide variety of passenger vehicles including various types of motor vehicles, watercraft, aircraft, trains, tanks, troops carriers and monorails. Additional applications and embodiments of the invention include manually powered vehicles such as bicycles and various skied vehicles. Other embodiments of the invention are directed to use in spacecraft and to use in animal-driven conveyances such as carriages, trailers, wagons and sleighs. In addition, various embodiments of the invention are adapted for use in amusement rides, balloons, houseboats, trams, elevators and construction vehicles.

Nor are the uses of the invention limited to vehicles. Other moving environments, such as trees and tree-houses, towers, pylons, docks, and skyscrapers, present useful applications for the invention.

It will be apparent to one of skill in the art that the invention described herein is a novel system, method and apparatus for preventing motion sickness. While the invention has been described with reference to specific preferred embodiments, it is not limited to these embodiments. The invention may be modified or varied in many ways and such modifications and variations as would be obvious to one of skill in the art are within the scope and spirit of the invention and are included within the scope of the following claims.

What is claimed is:

1. A motion sickness abatement device comprising:
   a video camera, said video camera being physically coupled to a vehicle, said video camera being adapted to primarily receive a first external image from a direction forwardly of, and external to said vehicle and to produce a signal corresponding to said first external image;
   a wireless communication device operatively coupled to said video camera, said wireless communication device being adapted to receive an image signal corresponding to said first external image from said video camera and to transmit a wireless signal corresponding to said image signal;
   a personal digital assistant disposed within said vehicle, said personal digital assistant being adapted to receive said wireless signal and, based on said wireless signal, display an image corresponding to said first external image and, concurrently, display a second image of a document unrelated to said first external image, based on data stored within said personal digital assistant, to a passenger whereby said second image may be read while said first and second images are viewed simultaneously, thereby minimizing motion sickness in said passenger.

2. A motion sickness abatement device as defined in claim 1 wherein said first image comprises a substantially stationary external point of reference.

3. A motion sickness abatement device as defined in claim 1 wherein said personal digital assistant is disposed within said vehicle and forwardly of said passenger.

4. A method of moderating motion sickness of a vehicle passenger comprising:
  physically coupling a video camera to a vehicle such that said video camera receives a first external image of said vehicle's environment primarily forwardly of said vehicle;
  operatively coupling said video camera to a wireless communication device, said wireless communication device being adapted to transmit a wireless signal corresponding to said first external image of said vehicle's environment within said vehicle;
  receiving said wireless signal at an electronic device within said vehicle, said electronic device having an electronic display;
  displaying by said electronic display, to said vehicle passenger, an image corresponding to said first external image; and
  concurrently displaying on said electronic display a document image, said document image being related to document data stored within said electronic device, so as to allow said vehicle passenger to view said first external image while reading said document image, and thereby moderate said motion sickness.

5. A method of moderating motion sickness of a vehicle passenger as defined in claim 4 wherein said electronic device comprises a personal electronic device.

* * * * *